(12) United States Patent
Zhang

(10) Patent No.: US 8,598,184 B2
(45) Date of Patent: Dec. 3, 2013

(54) PROTEIN KINASE INHIBITORS

(75) Inventor: Junhu Zhang, San Diego, CA (US)

(73) Assignee: Tiger Pharmatech, San Diego, CA (US)

( * ) Notice: Subject to any disclaimer, the term of this patent is extended or adjusted under 35 U.S.C. 154(b) by 0 days.

(21) Appl. No.: 12/919,216

(22) PCT Filed: Feb. 28, 2009

(86) PCT No.: PCT/US2009/035608
§ 371 (c)(1),
(2), (4) Date: Aug. 25, 2010

(87) PCT Pub. No.: WO2009/111354
PCT Pub. Date: Sep. 11, 2009

(65) Prior Publication Data
US 2010/0324074 A1     Dec. 23, 2010

Related U.S. Application Data

(60) Provisional application No. 61/067,889, filed on Mar. 3, 2008.

(51) Int. Cl.
*C07D 487/04* (2006.01)
*A61K 31/519* (2006.01)
*A61P 35/00* (2006.01)

(52) U.S. Cl.
USPC .................................. 514/261.1; 544/254

(58) Field of Classification Search
USPC .................................. 544/254; 514/261.1
See application file for complete search history.

(56) References Cited

U.S. PATENT DOCUMENTS

| | | | |
|---|---|---|---|
| 7,563,781 B2 * | 7/2009 | Ludovici et al. | 514/81 |
| 2011/0135600 A1 * | 6/2011 | Stieber et al. | 424/85.4 |

* cited by examiner

*Primary Examiner* — Susanna Moore
(74) *Attorney, Agent, or Firm* — Junhu Zhang

(57) ABSTRACT

The present invention is directed to low molecular weight and orally bioavailable 3H-[1,2,3]triazolo[4,5-d]pyrimidine derivatives, that are useful for treating cellular proliferative diseases, for treating disorders associated with MET activity, and for inhibiting the tyrosine kinase MET. The invention is also directed to compositions which comprise these compounds, and methods of using them to treat cancer in mammals.

14 Claims, 2 Drawing Sheets

Figure 1. Plasma Concentration-Time Curve of Example 5 in Male Rats Following Intravenous and Oral Administration (Mean ± SD)
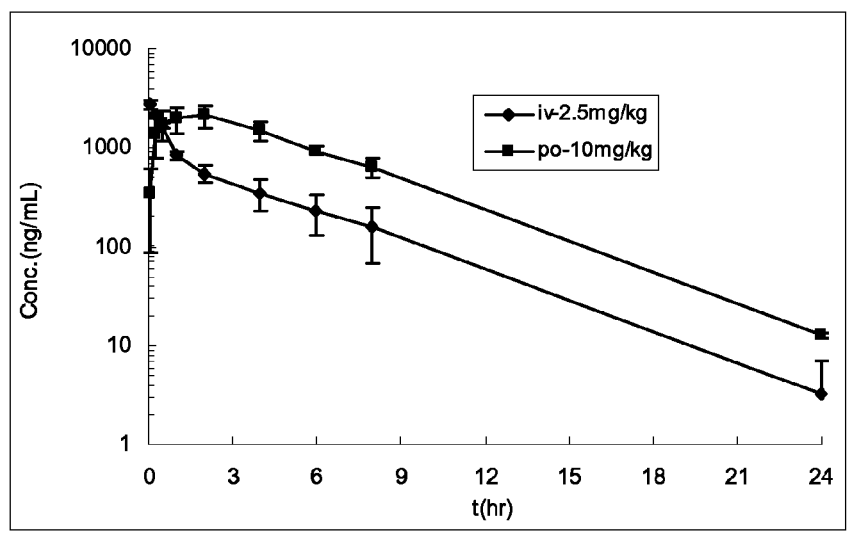

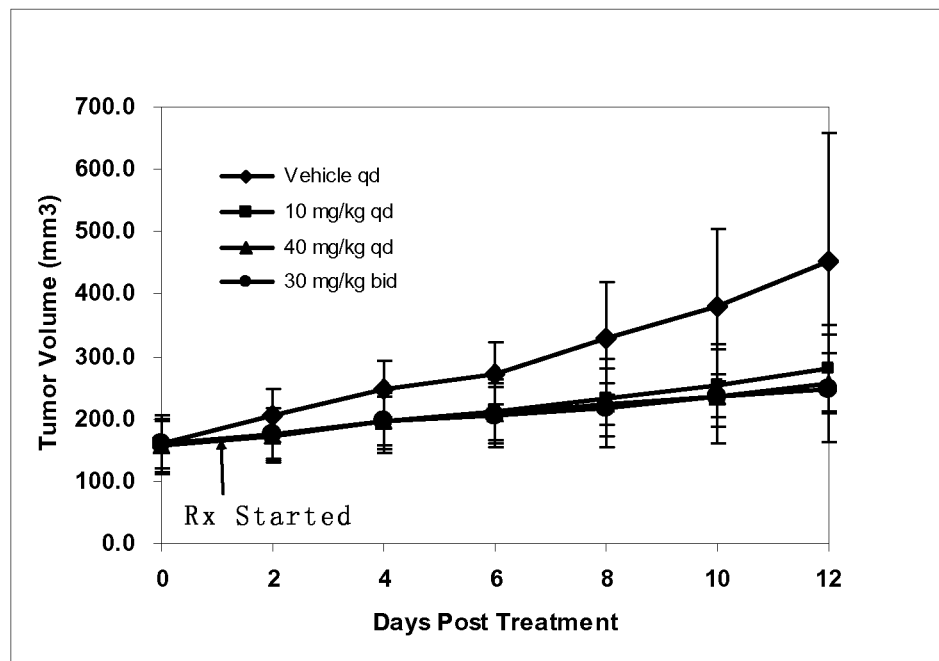
Figure 2. U87MG Growth Inhibition in Nude Mice with Example 5
(Values = Mean ± SEM, n = 8)

PROTEIN KINASE INHIBITORS

CROSS-REFERENCE TO RELATED APPLICATIONS

This is a national phase application which was filed Feb. 28, 2009, application number PCT/US2009/35608, which claims priority to U.S. Application No. 61/067,889, filed Mar. 3, 2008. The entire contents of these applications are incorporated herein by reference.

BACKGROUND OF THE INVENTION

This invention relates to 3H-[1,2,3]triazolo[4,5-d]pyrimidine compounds that are inhibitors of tyrosine kinases, in particular the receptor tyrosine kinase MET, and are useful in the treatment of cellular proliferative diseases, for example cancer, hyperplasias, restenosis, cardiac hypertrophy, immune disorders and inflammation.

Studies on signal transduction pathways have generated various promising molecular targets for therapeutic inhibition in cancer therapy. Receptor tyrosine kinases (RTK) represent an important class of such therapeutic targets. Recently, members of the MET proto-oncogene family, a subfamily of receptor tyrosine kinases, have drawn special attention to the association between invasion and metastasis.

The MET family, including MET (also referred to as c-Met) and RON receptors, can function as oncogenes like most tyrosine kinases. MET has been shown to be overexpressed and/or mutated in a variety of malignancies. A number of MET activating mutations, many of which are located in the tyrosine kinase domain, have been detected in various solid tumors and have been implicated in invasion and metastasis of tumor cells.

The c-Met proto-oncogene encodes the MET receptor tyrosine kinase. The MET receptor is a 190 kDa glycosylated dimeric complex composed of a 50 kDa alpha chain disulfide-linked to a 145 kDa beta chain. The alpha chain is found extracellularly while the beta chain contains extracellular, transmembrane and cytosolic domains. MET is synthesized as a precursor and is proteolytically cleaved to yield mature alpha and beta subunits. It displays structural similarities to semaphoring and plexins, a ligand-receptor family that is involved in cell-cell interaction.

The natural ligand for MET is hepatocyte growth factor (HGF), a disulfide linked heterodimeric member of the scatter factor family that is produced predominantly by mesenchymal cells and acts primarily on MET-expressing epithelial and endothelial cells in an endocrine and/or paraendocrine fashion. HGF has some homology to plasminogen. It is known that stimulation of MET via hepatocyte growth factor (also known as scatter factor, HGF/SF) results in a plethora of biological and biochemical effects in the cell. Activation of c-Met signaling can lead to a wide array of cellular responses including proliferation, survival, angiogenesis, wound healing, tissue regeneration, scattering, motility, invasion and branching morphogenesis. HGF/MET signaling also plays a major role in the invasive growth that is found in most tissues, including cartilage, bone, blood vessels, and neurons.

Various c-Met mutations have been well described in multiple solid tumors and some hematologic malignancies. The prototypic c-Met mutation examples are seen in hereditary and sporadic human papillary renal carcinoma (Schmidt, L. et al., *Nat. Tenet.* 1997, 16, 68-73; Jeffers, M. et al., *Proc. Nat. Acad. Sci* 1997, 94, 11445-11500). Other reported examples of c-Met mutations include ovarian cancer, childhood hepatocellular carcinoma, metastatic head and neck squamous cell carcinomas and gastric cancers. HGF/MET has been shown to inhibit anoikis, suspension-induced programmed cell death (apoptosis), in head and neck squamous cell carcinoma cells.

MET signaling is implicated in various cancers, especially renal. The nexus between MET and colorectal cancer has also been established. Analysis of c-Met expression during colorectal cancer progression showed that 50% of the carcinoma specimens analyzed expressed 5-50-fold higher levels of MET mRNA transcripts and protein versus the adjacent normal colonic mucosa. In addition, when compared to the primary tumor, 70% of colorectal cancer liver metastasis showed MET overexpression.

MET is also implicated in glioblastoma. High-grade malignant gliomas are the most common cancers of the central nervous system. Despite treatment with surgical resection, radiation therapy, and chemotherapy, the mean overall survival is <1.5 years, and few patients survive for >3 years. Human malignant gliomas frequently express both HGF and MET, which can establish an autocrine loop of biological significance. Glioma MET expression correlates with glioma grade, and an analysis of human tumor specimens showed that malignant gliomas have a 7-fold higher HGF content than low-grade gliomas. Multiple studies have demonstrated that human gliomas frequently co-express HGF and MET and that high levels of expression are associated with malignant progression. It was further shown that HGF-MET is able to activate Akt and protect glioma cell lines from apoptotic death, both in vitro and in vivo.

RON shares a similar structure, biochemical features, and biological properties with MET. Studies have shown RON overexpression in a significant fraction of breast carcinomas and colorectal adenocarcinomas, but not in normal breast epithelia or benign lesions. Cross-linking experiments have shown that RON and MET form a non-covalent complex on the cell surface and cooperate in intracellular signaling. RON and MET genes are significantly co-expressed in ovarian cancer cell motility and invasiveness. This suggests that co-expression of these two related receptors might confer a selective advantage to ovarian carcinoma cells during either tumor onset or progression.

A number of reviews on MET and its function as an oncogene have recently been published: *Nature Reviews/Cancer* 6:637-645 (2006); *Cancer and Metastasis Review* 22:309-325 (2003); *Nature Reviews/Molecular Cell Biology* 4:915-925 (2003); *Nature Reviews/Cancer* 2:289-300 (2002).

Since dysregulation of the HGF/MET signaling has been implicated as a factor in tumorgenesis and disease progression in many tumors, different strategies for therapeutic inhibition of this important RTK molecule should be investigated. Specific small molecule inhibitors against HGF/MET signaling and against RON/MET signaling have important therapeutic value for the treatment of cancers in which Met activity contributes to the invasive/metastatic phenotype.

SUMMARY OF THE INVENTION

The present invention relates to 3H-[1,2,3]triazolo[4,5-d] pyrimidine derivatives, that are useful for treating cellular proliferative diseases, for treating disorders associated with MET activity, and for inhibiting the receptor tyrosine kinase MET. The compounds of the invention may be illustrated by the Formula I and Formula II:

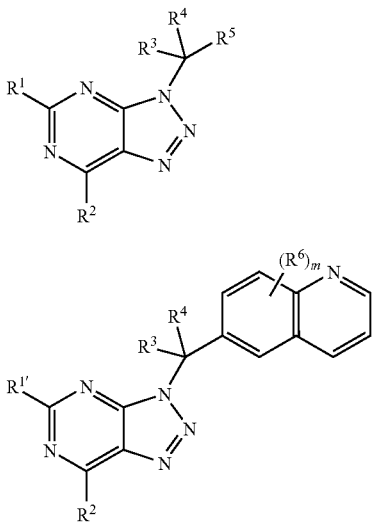

DESCRIPTION OF FIGURES

FIG. 1. Plasma Concentration-Time Curve of Example 5 in Male Rats Following Intravenous and Oral Administration (Mean±SD); and FIG. 2. U87MG Growth Inhibition in Nude Mice with Example 5 (Values=Mean±SEM, n=8).

DETAILED DESCRIPTION OF THE INVENTION

The compounds of this invention are useful in the inhibition of the receptor tyrosine kinase MET and are illustrated by a compound of Formula I or Formula II or partially deuterated Formula I or Formula II:

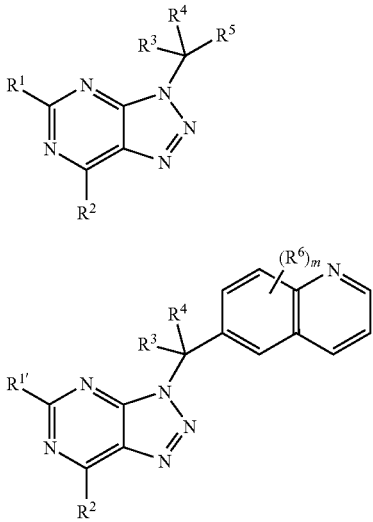

or a pharmaceutically acceptable salt thereof, wherein
$R^1$ is independently selected from $-O(CH_2)_nOR^{11}$, $-C(O)R^{11}$, $-C(O)OR^{11}$, $-C(O)NR^{11}R^{12}$, $C_3$-$C_8$ cycloalkyl, 3-8 membered heteroalicyclic, 3-8 membered heteroalicyclic-(3-8 membered heteroalicyclic), 8-10 membered heterobicyclic, 5-7 membered heteroaryl, $C_6$-$C_{10}$ aryl, $C_2$-$C_6$ alkenyl, and $C_2$-$C_6$ alkynyl wherein $C_3$-$C_8$ cycloalkyl, 3-8 membered heteroalicyclic, 8-10 membered heterobicyclic, 5-7 membered heteroaryl, $C_6$-$C_{10}$ aryl, $C_2$-$C_6$ alkenyl, and $C_2$-$C_6$ alkynyl are optionally substituted by one or more moieties selected from the group consisting of Br, Cl, F, $-(CH_2)_nCH(OR^{11})CH_3$, $-(CH_2)_nOR^{11}$, $-(CH_2)_nC(CH_3)_2OR^{11}$, $-C(O)R^{11}$, $-C(O)OR^{11}$, $-(CR^{11}R^{12})_nC(O)OR^{11}$, $-C(O)NR^{11}R^{12}$, $-(CR^{11}R^{12})_nC(O)NR^{11}R^{12}$, $-(CH_2)_nNR^{11}R^{12}$, $-S(O)_2R^{11}$, $-S(O)R^{11}$, $-S(O)_2NR^{11}R^{12}$, $-CF_3$, $-CF_2H$, $-(CH_2)_nNR^{11}C(O)NR^{11}R^{12}$, $-(CH_2)_nNR^{11}C(O)OR^{12}$, $-NR^{11}C(O)R^{12}$, $-NR^{11}C(O)OR^{12}$, $-NR^{11}S(O)_2R^{12}$, $-CN$, $-NO_2$, oxo, $C_1$-$C_6$ alkyl, $C_3$-$C_8$ cycloalkyl, $-(CH_2)_n$(3-8 membered heteroalicyclic), $-(CH_2)_n$(5-7 membered heteroaryl), $-(CH)_n(C_6$-$C_{10}$ aryl), $C_2$-$C_6$ alkenyl, and $C_2$-$C_6$ alkynyl;

$R^{1'}$ is independently selected from hydrogen, I, Br, Cl, F, $-O(CH_2)_nCH_3$, $-(CH_2)_nOR^{11}$, $-(CR^{13}R^{14})_nNR^{11}R^{12}$, $-NR^{11}C(O)OR^{13}$, $-NR^{11}R^{12}$, $-S(O)_2R^{11}$, $-S(O)R^{11}$, $-S(O)_2NR^{11}R^{12}$, $-CF_3$, $-CF_2H$, $-NR^{11}C(O)NR^{11}R^{12}$, $-NR^{11}C(O)R^{12}$, $-NR^{11}S(O)_2R^{12}$, $-N(CH_2)_n(C_3$-$C_8$ cycloalkyl), $-CN$, $-NO_2$, $C_1$-$C_6$ alkyl, or $R^1$ as defined above;

$R^2$ is H, halogen or $C_1$-$C_6$ alkyl;

$R^3$ and $R^4$ are independently selected from H, F, $CF_3$, $C_1$-$C_6$ alkyl;

or $R^3$ and $R^4$ can together form a $C_3$-$C_5$ cycloalkyl ring;

$R^5$ is a moiety of the formula:

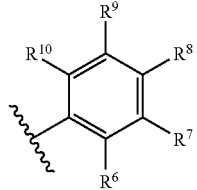

wherein $R^6$, $R^7$, $R^8$, $R^9$ and $R^{10}$ are independently selected from hydrogen, Br, Cl, F, $-(CH_2)_nR^{11}$, $-C(O)R^{11}$, $-C(O)OR^{11}$, $-C(O)NR^{11}R^{12}$, $NR^{11}R^{12}$, $S(O)_2R^{11}$, $-S(O)_nNR^{11}R^{12}$, $-CF_3$, $-CF_2H$, $NR^{11}C(O)NR^{11}R^{12}$, $NR^{11}C(OR)R^{12}$, $-NR^{11}SO_2R^{12}$, $-CN$, $-NO_2$, $C_1$-$C_6$ alkyl, $C_3$-$C_8$ cycloalkyl, 3-8 membered heteroalicyclic, 8-10 membered heterobicyclic, 5-7 membered heteroaryl, $C_6$-$C_{10}$ aryl, $C_2$-$C_6$ alkenyl, and $C_2$-$C_6$ alkynyl wherein $C_1$-$C_6$ alkyl, $C_3$-$C_8$ cycloalkyl, 3-8 membered heteroalicyclic, 8-10 membered heterobicyclic, 5-7 membered heteroaryl, $C_6$-$C_{10}$ aryl, $C_2$-$C_6$ alkenyl, and $C_2$-$C_6$ alkynyl are optionally substituted by one or more moieties selected from the group consisting of Br, Cl, F, $-(CH_2)_nOR^{11}$, $-C(O)R^{11}$, $-C(O)OR^{11}$, $-C(O)NR^{11}R^{12}$, $-NR^{11}R^{12}$, $-S(O)_2R^{11}$, $-S(O)R^{11}$, $-S(O)_2NR^{11}R^{12}$, $-CF_3$, $-CF_2H$, $-NR^{11}C(O)NR^{11}R^{12}$, $NR^{11}C(O)R^{12}$, $-NR^{11}S(O)_2R^{12}$, $-CN$, $-NO_2$, oxo, $C_1$-$C_6$alkyl, $C_3$-$C_8$ cycloalkyl, $C_3$-$C_8$ heteroalicyclic, 5-7 membered heteroaryl, $C_6$-$C_{10}$ aryl, $C_2$-$C_6$ alkenyl, and $C_2$-$C_6$ alkynyl; or $R^8$ and $R^9$, or $R^9$ and $R^{10}$ combine to form a ring selected from saturated $C_4$-$C_8$ cycloalkyl, unsaturated $C_5$-$C_8$ cycloalkyl, 3-8 membered heteroalicyclic, 5-7 membered heteroaryl and $C_6$-$C_{10}$ aryl, wherein said ring is optionally substituted by one or more moieties selected from the group consisting of Br, Cl, F, $-(CH_2)_nOR^{11}$, $-C(O)R^{11}$, $-C(O)OR^{11}$, $-C(O)NR^{11}R^{12}$, $-NR^{11}R^{12}$, $-S(O)_2R^{11}$, $-S(O)R^{11}$, $-S(O)_2NR^{11}R^{12}$, $-CF_3$, $-CF_2H$, $-NR^{11}C(O)NR^{11}R^{12}$, $NR^{11}C(O)R^{12}$, $-NR^{11}S(O)_2R^{12}$, $-CN$, $-NO_2$, oxo, $C_1$-$C_6$ alkyl, $C_3$-$C_8$ cycloalkyl, $C_3$-$C_8$ heteroalicyclic, 5-7 membered heteroaryl, $C_6$-$C_{10}$ aryl, $C_2$-$C_6$ alkenyl, and $C_2$-$C_6$ alkynyl;

wherein if m is greater than 1, then each $R^6$ is independently selected from hydrogen, Br, Cl, F, —$(CH_2)_nOR^{11}$, —$C(O)R^{11}$, $C(O)OR^{11}$, —$C(O)NR^{11}R^{12}$, $NR^{11}R^{12}$, —$S(O)_2R^{11}$, —$S(O)R^{11}$, —$S(O)_2NR^{11}R^{12}$, —$CF_3$, —$CF_2H$, —$NR^{11}C(O)NR^{11}R^{12}$, —$NR^{11}C(O)R^{12}$, —$NR^{11}SO_2R^{12}$, —$CN$, —$NO_2$, $C_1$-$C_6$ alkyl, $C_3$-$C_8$ cycloalkyl, 3-8 membered heteroalicyclic, 8-10 membered heterobicyclic, 5-7 membered heteroaryl, $C_6$-$C_{10}$ aryl, $C_2$-$C_6$ alkenyl, and $C_2$-$C_6$ alkynyl wherein $C_1$-$C_6$ alkyl, $C_3$-$C_8$ cycloalkyl, 3-8 membered heteroalicyclic, 8-10 membered heterobicyclic, 5-7 membered heteroaryl, $C_6$-$C_{10}$ aryl, $C_2$-$C_6$ alkenyl, and $C_2$-$C_6$ alkynyl are optionally substituted by one or more moieties selected from the group consisting of Br, Cl, F, —$(CH_2)_nOR^{11}$, —$C(O)R^{11}$, —$C(O)OR^{11}$, —$C(O)NR^{11}R^{12}$, —$NR^{11}R^{12}$, —$S(O)_2R^{11}$, —$S(O)_2NR^{11}R^{12}$, —$CF_3$, —$CF_2H$, —$NR^{11}C(O)NR^{11}R^{12}$, —$NR^{11}C(O)R^{12}$, $NR^{11}S(O)_2R^{12}$, —$CN$, —$NO_2$, oxo, $C_1$-$C_6$ alkyl, $C_3$-$C_8$ cycloalkyl, $C_3$-$C_8$ heteroalicyclic, 5-7 membered heteroaryl, $C_6$-$C_{10}$ aryl, $C_2$-$C_6$ alkenyl, and $C_2$-$C_6$ alkynyl;

$R^{11}$ and $R^{12}$ are independently selected from H, —$(CH_2)_nOR^{13}$, —$(CH_2)_nC(CH_3)_2OR^{13}$, —$CHR^{13}(CH_2)_nOR^{14}$, —$C(O)OR^{13}$, —$C(O)OR^{13}$, —$(CH_2)_nCHR^{13}OR^{14}$, —$C(CH_3)_2(CH_2)_nOR^{13}$, —$CH_2CF_2H$, —$(CH_2)_nC(CH_3)_2NR^{13}R^{14}$, —$(CH_2)_nNR^{13}R^{14}$, —$(CH_2)_nCHOR^{13}(CH_2)_nOR^{14}$, —$(CH_2)_n(NR^{13}R^{14})C(O)NR^{13}R^{14}$, —$(CH_2)_nS(O)_2R^{13}$, —$(CH_2)_nC(O)NR^{13}R^{14}$, —$NR^{13}(CH_2)_n$(5-7 membered heteroaryl), —$NR^{13}(CH_2)_n$(3-8 membered heterocycle), —$(CH_2)_n$(8-10 membered heterobicyclic), —$(CH_2)_n$(3-8 membered heteroalicyclic), $C_1$-$C_6$ alkyl, $C_3$-$C_8$ cycloalkyl, $C_6$-$C_{10}$ aryl, $C_2$-$C_6$ alkenyl and $C_2$-$C_6$ alkynyl, wherein said 5-7 membered heteroaryl, 3-8 membered heterocycle and 8-10 membered heterobicyclic are optionally substituted by one or more moieties selected from the group consisting of —$(CH_2)_nOR^{13}$, $C_1$-$C_6$ alkyl, $C_3$-$C_8$ cycloalkyl, $C_6$-$C_{10}$ aryl, $C_2$-$C_6$ alkenyl, 3-8 membered heteroalicyclic and $C_2$-$C_6$ alkynyl; or when $R^{11}$ and $R^{12}$ are attached to the same atom, $R^{11}$ and $R^{12}$ optionally combine to form a 3-8 membered heteroalicyclic ring;

$R^{13}$ and $R^{14}$ are independently selected from H, $C_1$-$C_6$ alkyl, —$C(O)CH_3$, $C_3$-$C_8$ cycloalkyl, $C_6$-$C_{10}$ aryl, $C_2$-$C_6$ alkenyl, 5-7 membered heteroaryl and $C_2$-$C_6$ alkynyl, wherein said 5-7 membered heteroaryl is optionally substituted by one or more moieties selected from the group consisting of $C_1$-$C_6$ alkyl, $C_3$-$C_8$ cycloalkyl, $C_6$-$C_{10}$ aryl, $C_2$-$C_6$ alkenyl, and $C_2$-$C_6$ alkynyl; or when $R^{13}$ and $R^{14}$ are attached to the same atom $R^{13}$ and $R^{14}$ optionally combine to form a 3-8 membered heteroalicyclic ring;

each n is independently 0, 1, 2, 3 or 4;

m is 0, 1, 2, 3, 4 or 5.

The present invention contemplates each of the following embodiments separately or in connection with any other embodiment described herein except where an inconsistency in describing the present invention might occur. Based on the present disclosure the person having ordinary skill in the art will readily appreciate what such inconsistencies might be.

In another embodiment, $R^{1'}$ is independently selected from hydrogen, I, Cl, —$O(CH_2)_nCH_3$, —$(CH_2)_nOR^{11}$, $(CR^{13}R^{14})_nNR^{11}R^{12}$, —$NR^{11}C(O)OR^{13}$, —$NR^{11}R^{12}$, —$S(O)_2R^{11}$, —$S(O)R^{11}$, —$S(O)_2NR^{11}R^{12}$, —$CF_3$, —$CF_2H$, —$NR^{11}C(O)NR^{11}R^{12}$, —$NR^{11}C(O)R^{12}$, —$NR^{11}S(O)_2R^{12}$, —$N(CH_2)_n$ ($C_3$-$C_8$ cycloalkyl), —$CN$, —$NO_2$, $C_1$-$C_6$ alkyl, or $R^1$ as defined above.

In another embodiment, $R^{1'}$ is $R^1$, wherein $R^1$ as defined above.

In another embodiment, $R^1$ is independently selected from —$C(O)NR^{11}R^{12}$, 3-8 membered heteroalicyclic, 3-8 membered heteroalicyclic-(3-8 membered heteroalicyclic), 8-10 membered heterobicyclic, 5-7 membered heteroaryl, $C_6$-$C_{10}$ aryl and $C_2$-$C_6$ alkenyl, wherein 3-8 membered heteroalicyclic, 3-8 membered heteroalicyclic-(3-8 membered heteroalicyclic), 8-10 membered heterobicyclic, 5-7 membered heteroaryl, $C_6$-$C_{10}$ aryl and $C_2$-$C_6$ alkenyl are optionally substituted by one or more moieties selected from the group consisting of Br, Cl, F, —$(CH_2)_nCH(OR^{11})CH_3$, —$(CH_2)_nOR^{11}$, —$(CH_2)_nC(CH_3)_2OR^{11}$, —$(CH_2)_n$(3-8 membered heteroalicyclic), —$C(O)R^{11}$, —$C(O)OR^{11}$, —$(CR^{11}R^{12})_nC(O)OR^{11}$, —$C(O)NR^{11}R^{12}$, $(CR^{11}R^{12})_nC(O)NR^{11}R^{12}$, —$(CH_2)_nNR^{11}R^{12}$, —$S(O)_2R^{11}$, —$S(O)R^{11}$, $S(O)_2NR^{11}R^{12}$, —$CF_3$, —$CF_2H$, —$(CH_2)_nNR^{11}C(O)NR^{11}R^{12}$, —$(CH_2)_nNR^{11}C(O)OR^{12}$, —$NR^{11}C(O)R^{12}$, —$NR^{11}C(O)OR^{12}$, —$NR^{11}S(O)_2R^{12}$, —$CN$, —$NO_2$, oxo, $C_1$-$C_6$ alkyl, $C_3$-$C_8$ cycloalkyl, —$(CH_2)_n$(3-8 membered heteroalicyclic), —$(CH_2)_n$(5-7 membered heteroaryl), —$(CH_2)_n$($C_6$-$C_{10}$ aryl), $C_2$-$C_6$ alkenyl, and $C_2$-$C_6$ alkynyl.

In another embodiment, $R^1$ is independently selected from 3-8 membered heteroalicyclic, 3-8 membered heteroalicyclic-(3-8 membered heteroalicyclic), 8-10 membered heterobicyclic, 5-7 membered heteroaryl, $C_6$-$C_{10}$ aryl and $C_2$-$C_6$ alkenyl, wherein 3-8 membered heteroalicyclic, 3-8 membered heteroalicyclic-(3-8 membered heteroalicyclic), 8-10 membered heterobicyclic, 5-7 membered heteroaryl, $C_6$-$C_{10}$ aryl and $C_2$-$C_6$ alkenyl are optionally substituted by one or more moieties selected from the group consisting of Br, Cl, F, —$(CH_2)_nCH(OR^{11})CH_3$, —$(CH_2)_nOR^{11}$, —$(CH_2)_nC(CH_3)_2OR^{11}$, —$(CH_2)_n$(3-8 membered heteroalicyclic), —$C(O)R^{11}$, —$C(O)OR^{11}$, —$(CR^{11}R^{12})_nC(O)OR^{11}$, —$C(O)NR^{11}R^{12}$, —$(CR^{11}R^{12})_nC(O)NR^{11}R^{12}$, —$(CH_2)_nNR^{11}R^{12}$, —$S(O)_2R^{11}$, —$S(O)R^{11}$, —$S(O)_2NR^{11}R^{12}$, —$CF_3$, —$CF_2H$, —$(CH_2)_nNR^{11}C(O)NR^{11}R^{12}$, $(CH_2)_nNR^{11}C(O)OR^{12}$, —$NR^{11}C(O)OR^{12}$, $NR^{11}C(O)OR^{12}$, —$NR^{11}S(O)_2R^{12}$, —$CN$, —$NO_2$, oxo, $C_1$-$C_6$ alkyl, $C_3$-$C_8$ cycloalkyl, —$(CH_2)_n$(3-8 membered heteroalicyclic), —$(CH_2)_n$(5-7 membered heteroaryl), —$(CH_2)_n$($C_6$-$C_{10}$ aryl), $C_2$-$C_6$ alkenyl, and $C_2$-$C_6$ alkynyl.

In another embodiment, $R^1$ is selected from 8-10 membered heterobicyclic, 5-7 membered heteroaryl, $C_6$-$C_{10}$ aryl and $C_2$-$C_6$ alkenyl, wherein 8-10 membered heterobicyclic, 5-7 membered heteroaryl, $C_6$-$C_{10}$ aryl and $C_2$-$C_6$ alkenyl are optionally substituted by one or more moieties selected from the group consisting of Br, Cl, F, —$(CH_2)_nCH(OR^{11})CH_3$, —$(CH_2)_nOR^{11}$, —$(CH_2)_nC(CH_3)_2OR^{11}$, —$(CH_2)_n$(3-8 membered heteroalicyclic), —$C(O)R^{11}$, —$C(O)OR^{11}$, —$(CR^{11}R^{12})_nC(O)OR^{11}$, —$C(O)NR^{11}R^{12}$, —$(CR^{11}R^{12})_nC(O)NR^{11}R^{12}$, —$(CH_2)_nNR^{11}R^{12}$, —$S(O)_2R^{11}$, —$S(O)R^{11}$, —$S(O)_2NR^{11}R^{12}$, —$CF_3$, —$CF_2H$, —$(CH_2)_nNR^{11}C(O)NR^{11}R^{12}$, —$(CH_2)_nNR^{11}C(O)OR^{12}$, —$NR^{11}C(O)R^{12}$, —$NR^{11}C(O)OR^{12}$, —$NR^{11}S(O)_2R^{12}$, —$CN$, —$NO_2$, oxo, $C_1$-$C_6$ alkyl, $C_3$-$C_8$ cycloalkyl, —$(CH_2)_n$(3-8 membered heteroalicyclic), —$(CH_2)_n$(5-7 membered heteroaryl), —$(CH_2)_n$($C_6$-$C_{10}$ aryl), $C_2$-$C_6$ alkenyl, and $C_2$-$C_6$ alkynyl.

In another embodiment, $R^1$ is a 5-7 membered heteroaryl optionally substituted by one or more moieties selected from the group consisting of Br, Cl, F, —$(CH_2)_nCH(OR^{11})CH_3$, —$(CH_2)_nOR^{11}$, —$(CH_2)_nC(CH_3)_2OR^{11}$, —$(CH_2)_n$(3-8 membered heteroalicyclic), —$C(O)R^{11}$, —$C(O)OR^{11}$ —$(CR^{11}R^{12})_nC(O)OR^{11}$, —$C(O)NR^{11}R^{12}$, —$(CR^{11}R^{12})_nC(O)NR^{11}R^{12}$, —$(CH_2)_nNR^{11}R^{12}$, —$S(O)_2R^{11}$, —$S(O)R^{11}$, —$S(O)_2NR^{11}R^{12}$, —$CF_3$, —$CF_2H$, —$(CH_2)_nNR^{11}C(O)NR^{11}R^{12}$, —$(CH_2)_nNR^{11}C(O)OR^{12}$, —$NR^{11}C(O)R^{12}$, —$NR^{11}C(O)OR^{12}$, —$NR^{11}S(O)_2R^{12}$, —$CN$, —$NO_2$, oxo, $C_1$-$C_6$ alkyl, $C_3$-$C_8$ cycloalkyl, —$(CH_2)_n$(3-8 membered heteroalicyclic), —(CH$_2$)$_n$(5-7 membered heteroaryl), —(CH$_2$)$_n$(C$_6$-C$_{10}$ aryl), C$_2$-C$_6$ alkenyl, and C$_2$-C$_6$ alkynyl.

In another embodiment, R$^8$ and R$^9$ combine to form a ring selected from saturated C$_4$-C$_8$ cycloalkyl, unsaturated C$_5$-C$_8$ cycloalkyl, 3-8 membered heteroalicyclic, 5-7 membered heteroaryl and C$_6$-C$_{10}$ aryl, wherein said ring is optionally substituted by one or more moieties selected from the group consisting of Br, Cl, F, —(CH$_2$)$_n$OR$^{11}$, —C(O)R$^{11}$, —C(O)OR$^{11}$, —C(O)NR$^{11}$R$^{12}$, —NR$^{11}$R$^{12}$, —S(O)$_2$R$^{11}$, —S(O)R$^{11}$, —S(O)$_2$NR$^{11}$R$^{12}$, —CF$_3$, —CF$_2$H, —NR$^{11}$C(O)NR$^{11}$R$^{12}$, —NR$^{11}$C(O)R$^{12}$, —NR$^{11}$S(O)$_2$R$^{12}$, —CN, —NO$_2$, oxo, C$_1$-C$_6$ alkyl, C$_3$-C$_8$ cycloalkyl, C$_3$-C$_8$ heteroalicyclic, 5-7 membered heteroaryl, C$_6$-C$_{10}$ aryl, C$_2$-C$_6$ alkenyl, and C$_2$-C$_6$ alkynyl.

In a further embodiment, R$^{10}$ is H. In another embodiment, R$^2$ is H. In another embodiment, R$^3$ and R$^4$ are independently selected from H, F, CF$_3$, CH$_3$. In another embodiment, R$^3$ and R$^4$ are H. In another embodiment, R$^3$ and R$^4$ are F. In another embodiment, R$^3$ is H, R$^4$ is CH$_3$. In another embodiment, R$^3$ is CH$_3$ and R$^4$ is H. In a further embodiment, R$^3$ and R$^4$ can together form a C$_3$-C$_5$ cycloalkyl ring. In another embodiment, R$^6$ and R$^7$ are H.

In another embodiment, R$^5$ selected from

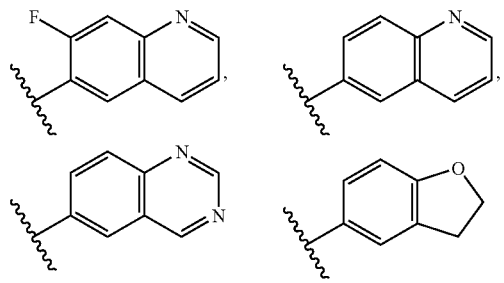

In another embodiment, R$^5$ is

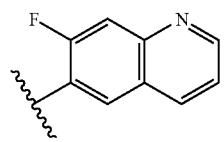 [SMILES: *c1cc2cccnc2cc1F]

In another embodiment, R$^5$ is

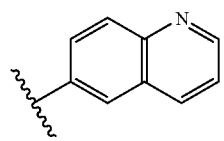 [SMILES: *c1ccc2ncccc2c1]

In another embodiment R$^5$ is

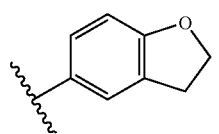 [SMILES: *c1ccc2c(c1)CCO2]

In another embodiment, the present invention relates to a compound selected from 6-((5-chloro-3H-[1,2,3]triazolo[4,5-d]pyrimidin-3-yl)methyl)quinoline, 3-(quinolin-6-ylmethyl)-3H-[1,2,3]triazolo[4,5-d]pyrimidin-5-amine, 6-((5-iodo-3H-[1,2,3]triazolo[4,5-d]pyrimidin-3-yl)methyl)quinoline, 6-((5-(1-methyl-1H-pyrazol-4-yl)-3H-[1,2,3]triazolo[4,5-d]pyrimidin-3-yl)methyl)quinoline, 2-(4-(3-(quinolin-6-ylmethyl)-3H-[1,2,3]triazolo[4,5-d]pyrimidin-5-yl)-1H-pyrazol-1-yl)ethanol, or a pharmaceutically acceptable salt thereof.

In a further aspect, the invention relates to pharmaceutical composition comprising a compound of the Formula I or Formula II or a pharmaceutically acceptable salt thereof, and a pharmaceutically acceptable excipient.

In a further aspect, the invention relates to the use of a compound of the Formula I or Formula II or a pharmaceutically acceptable salt thereof, for the manufacture of a medicament to treat a c-Met related disorder in a mammal.

In a further aspect, the invention relates to the use of a compound of the Formula I or Formula II or a pharmaceutically acceptable salt thereof, for the manufacture of medicament for the treatment of cancer in a mammal.

In a further aspect, the invention relates to the use of a compound of the Formula I or Formula II, wherein the cancer is selected from breast cancer, lung cancer, colorectal cancer, prostate cancer, pancreatic cancer, glioma, liver cancer, gastric cancer, head cancer, neck cancer, melanoma, renal cancer, leukemia, myeloma, and sarcoma.

In a further aspect, the invention relates to a method of treating a mammal having a c-Met related disorder, comprising administering to the mammal a therapeutically effective amount of a compound of the Formula I or Formula II or with a pharmaceutically acceptable salt thereof.

In a further aspect, the invention relates to a method of treating a mammal having cancer, comprising administering to the mammal a therapeutically effective amount of a compound of the Formula I or Formula II or with a pharmaceutically acceptable salt thereof.

In a further aspect, the invention relates to a method of treating cancer where the cancer is selected from breast cancer, lung cancer, colorectal cancer, prostate cancer, pancreatic cancer, glioma, liver cancer, gastric cancer, head cancer, neck cancer, melanoma, renal cancer, leukemia, myeloma, and sarcoma. In a further embodiment the mammal is a human. In a further embodiment the mammal is a canine.

DEFINITIONS

"Pharmaceutically acceptable salt" refers to those salts, which retain the biological effectiveness and properties of the parent compound. Such salts include: acid addition salt which is obtained by reaction of the free base of the parent compound with inorganic acids such as hydrochloric acid, hydrobromic acid, hydroiodic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, benzenesulfonic acid (besylate), benzoic acid, camphorsulfonic add, citric acid, fumaric acid, gluconic acid, glutamic acid, isethionic acid, lactic acid, mandelic acid, mucic acid, pamoic acid, pantothenic acid, succinic acid, or malonic acid and the like, preferably hydrochloric acid or (L)-malic acid; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

"Pharmaceutically acceptable excipient" or "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils, polyethylene glycols, diluents, granulating agents, lubricants, binders, disintegrating agents, and the like.

A "pharmaceutical composition" refers to a mixture of one or more of the compounds described herein, or physiologically acceptable salts thereof, with other chemical components, such as physiologically acceptable carriers and excipients. The purpose of a pharmaceutical composition is to facilitate administration of a compound to an organism.

As used herein, a "physiologically acceptable carrier" refers to a carrier or diluent that does not cause significant irritation to an organism and does not abrogate the biological activity and properties of the administered compound.

The term "method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

As used herein, the term "modulation" or "modulating" refers to the alteration of the catalytic activity of c-Met. In particular, modulating refers to the activation of the catalytic activity of c-Met, preferably the activation or inhibition of the catalytic activity of c-Met, depending on the concentration of the compound or salt to which c-Met is exposed or, more preferably, the inhibition of the catalytic activity of c-Met.

The term "contacting" as used herein refers to bringing a compound of this invention and c-Met together in such a manner that the compound can affect the catalytic activity of c-Met, either directly, i.e., by interacting with c-Met itself, or indirectly, i.e., by interacting with another molecule on which the catalytic activity of c-Met is dependent. Such "contacting" can be accomplished in vitro, i.e., in a test tube, a Petri dish or the like. In a test tube, contacting may involve only a compound and c-Met or it may involve whole cells. Cells may also be maintained or grown in cell culture dishes and contacted with a compound in that environment. In this context, the ability of a particular compound to affect a c-Met related disorder, i.e., the $IC_{50}$ of the compound, defined below, can be determined before use of the compounds in vivo with more complex living organisms is attempted. For cells outside the organism, multiple methods exist, and are well-known to those skilled in the art, to get c-Met in contact with the compounds including, but not limited to, direct cell microinjection and numerous transmembrane carrier techniques.

The term "deuterated" refers to replace hydrogen by deuterium.

"In vitro" refers to procedures performed in an artificial environment such as, e.g., without limitation, in a test tube or culture medium. The skilled artisan will understand that, for example, isolated c-Met may be contacted with a modulator in an in vitro environment. Alternatively, an isolated cell may be contacted with a modulator in an in vitro environment.

As used herein, "in vivo" refers to procedures performed within a living organism such as, without limitation, a mouse, rat, rabbit, ungulate, bovine, equine, porcine, canine, feline, primate, or human.

As used herein, "c-Met related disorder," refers to a condition characterized by inappropriate, i.e., under-activity or, more commonly, over-activity of the c-Met catalytic activity. A "c-Met related disorder" also refers to a condition where there may be a mutation in the gene that produces c-Met, which, in turn, produces a c-Met that has an increased or decreased c-Met catalytic activity.

Inappropriate catalytic activity can arise as the result of either: (1) c-Met expression in cells which normally do not express c-Met, (2) increased c-Met expression leading to unwanted cell proliferation, differentiation and/or growth, or, (3) decreased c-Met expression leading to unwanted reductions in cell proliferation, differentiation and/or growth. Over-activity of a c-Met refers to either amplification of the gene encoding a c-Met or production of a level of c-Met activity which can correlate with a cell proliferation, differentiation and/or growth disorder (that is, as the level of the c-Met increases, the severity of one or more of the symptoms of the cellular disorder increases). Under-activity is, of course, the converse, wherein the severity of one or more symptoms of a cellular disorder increase as the level of the c-Met activity decreases.

As used herein, the terms "treat", "treating" and "treatment" refer to a method of alleviating or abrogating a c-Met mediated cellular disorder and/or its attendant symptoms. With regard particularly to cancer, these terms simply mean that the life expectancy of an individual affected with a cancer will be increased or that one or more of the symptoms of the disease will be reduced.

The term "organism" refers to any living entity comprised of at least one cell. A living organism can be as simple as, for example, a single eukaryotic cell or as complex as a mammal In a preferred aspect, the organism is a mammal In a particularly preferred aspect, the mammal is a human being.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

By "monitoring" is meant observing or detecting the effect of contacting a compound with a cell expressing a c-Met. The observed or detected effect can be a change in cell phenotype, in the catalytic activity of c-Met or a change in the interaction of c-Met with a natural binding partner. Techniques for observing or detecting such effects are well-known in the art. For example, the catalytic activity of c-Met may be observed by determining the rate or amount of phosphorylation of a target molecule.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

A "natural binding partner" refers to a polypeptide that binds to a c-Met in a cell. Natural binding partners can play a role in propagating a signal in a c-Met-mediated signal transduction process. A change in the interaction of the natural binding partner with c-Met can manifest itself as an increased or decreased concentration of the c-Met/natural binding partner complex and, as a result, in an observable change in the ability of c-Met to mediate signal transduction.

As used herein, "administer" or "administration" refers to the delivery of a compound or a salt of the present invention or of a pharmaceutical composition containing a compound or salt of this invention to an organism for the purpose of prevention or treatment of a c-Met-related disorder. The terms "abnormal cell growth" and "hyperproliferative disorder" are used interchangeably in this application.

"Abnormal cell growth", as used herein, refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase.

"Alkyl" refers to a saturated aliphatic hydrocarbon including straight chain or branched chain. Preferably, the alkyl group has 1 to 20 carbon atoms (whenever a numerical range; e.g., "1-20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 6 carbon atoms. The alkyl group may be substituted or unsubstituted. When substituted, each substituent group is preferably one or more individually selected from halogen, -hydroxy, —COR', —COOR', —OCOR', —CONRR', —RNCOR', —NRR', —CN, —NO$_2$, —CF$_3$ —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' can be independently H, alkyl, or aryl, wherein alkyl or aryl may be further substituted with halogen, $(CH_2)_nN(R'')_2$, $(CH_2)_nCO_2R''$, $(CH_2)_nOR''$, $(CH_2)_nOC(O)R''$, alkoxycarbonyl, aryloxycarbonyl, aminocarbonyl, a heteroalicyclic ring, aryl, alkoxy, —OCF$_3$, aryloxy, C(O)NH$_2$ or heteroaryl. R'' can be H, alkyl or aryl. n is 0-3.

"Alkenyl" refers to an aliphatic hydrocarbon having at least one carbon-carbon double bond, including straight chain, branched chain or cyclic groups having at least one carbon-carbon double bond. Preferably, the alkenyl group has 2 to 20 carbon atoms (whenever a numerical range; e.g., "2-20", is stated herein, it means that the group, in this case the alkenyl group, may contain 2 carbon atoms, 3 carbon atoms, etc. up to and including 20 carbon atoms). More preferably, it is a medium size alkenyl having 2 to 10 carbon atoms. Most preferably, it is a lower alkenyl having 2 to 6 carbon atoms. Examples, without limitation, of alkenyl groups include 1-propenyl, 1- and 2-butenyl, etc. The alkenyl group may be substituted or unsubstituted. When substituted, each substituent group is preferably one or more individually selected from halogen, -hydroxy, —COR', —COOR', —OCOR', —CONRR', —RNCOR', —NRR', —CN, —NO$_2$, —CF$_3$, —SR', SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

"Alkynyl" refers to an aliphatic hydrocarbon having at least one carbon-carbon triple bond, including straight chain, branched chain or cyclic groups having at least one carbon-carbon triple bond. Preferably, the alkenyl group has 2 to 20 carbon atoms (whenever a numerical range; e.g., "2-20", is stated herein, it means that the group, in this case the alkynyl group, may contain 2 carbon atoms, 3 carbon atoms, etc. up to and including 20 carbon atoms). More preferably, it is a medium size alkynyl having 2 to 10 carbon atoms. Most preferably, it is a lower alkynyl having 2 to 6 carbon atoms. Examples, without limitation, of alkynyl groups include 1-propynyl, 1- and 2-butynyl, etc. The alkynyl group may be substituted or unsubstituted. When substituted, each substituent group is preferably one or more individually selected from halogen, —hydroxy, —COR', —COOR', —OCOR', —CONRR', —RNCOR', —NRR', —CN, —NO$_2$, —CF$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

A "cycloalkyl" or an "alicyclic" group refers to an all-carbon monocyclic or fused ring (i.e., rings which share an adjacent pair of carbon atoms) group wherein one of more of the rings does not have a completely conjugated pi-electron system. Preferably, the cycloalkyl group has from 3-8 carbon atoms in the ring(s). Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, each substituent group is preferably one or more individually selected from halogen, —hydroxy, —COR', —COOR', —OCOR', —CONRR', —RNCOR', —NRR', —CN, —NO$_2$, —CF$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

An "aryl" group refers to an all-carbon monocyclic or fused-ring polycyclic (i.e., rings which share adjacent pairs of carbon atoms) groups having a completely conjugated pi-electron system. Preferably, the aryl group has from 6 to 12 carbon atoms in the ring(s). Examples, without limitation, of aryl groups are phenyl, naphthalenyl and anthracenyl. The aryl group may be substituted or unsubstituted. When substituted, each substituted group is preferably one or more selected halogen, hydroxy, alkoxy, aryloxy, —COW, —COOR', —OCOR', —CONRR', —RNCOR', —NRR', —CN, —NO$_2$, —CF$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

As used herein, a "heteroaryl" group refers to a monocyclic group having in the ring one or more atoms selected from the group consisting of nitrogen, oxygen and sulfur with the proviso that heteroaryl groups containing highly unstable heteroatom arrangements, such as O—O, O—O—O and the like, are not contemplated by the present invention. One of ordinary skill in the art will recognize unstable groups that are not contemplated by the invention. In addition, the heteroaryl group has a completely conjugated pi-electron system. Preferably, the heteroaryl group has from 5 to 7 ring atoms. Examples of typical monocyclic heteroaryl groups include, but are not limited to:

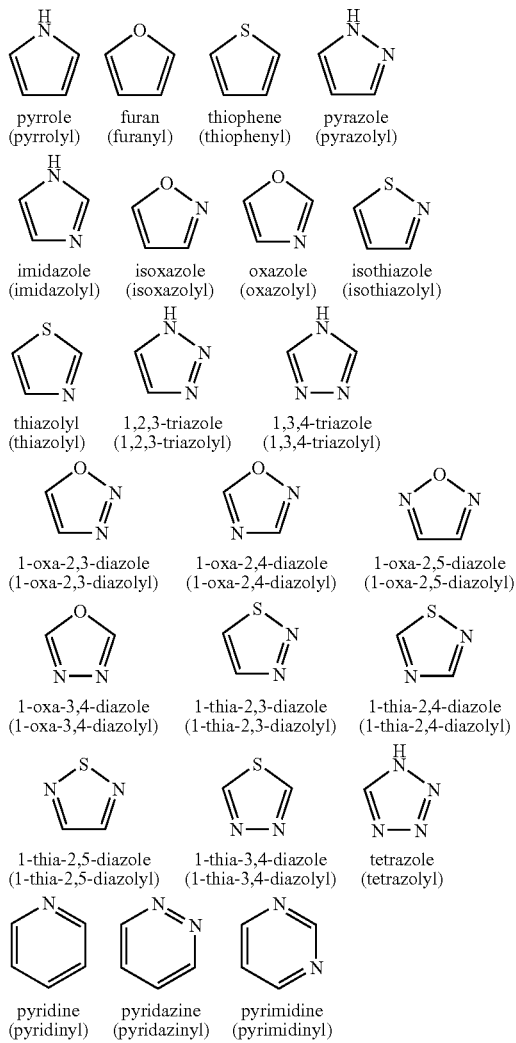

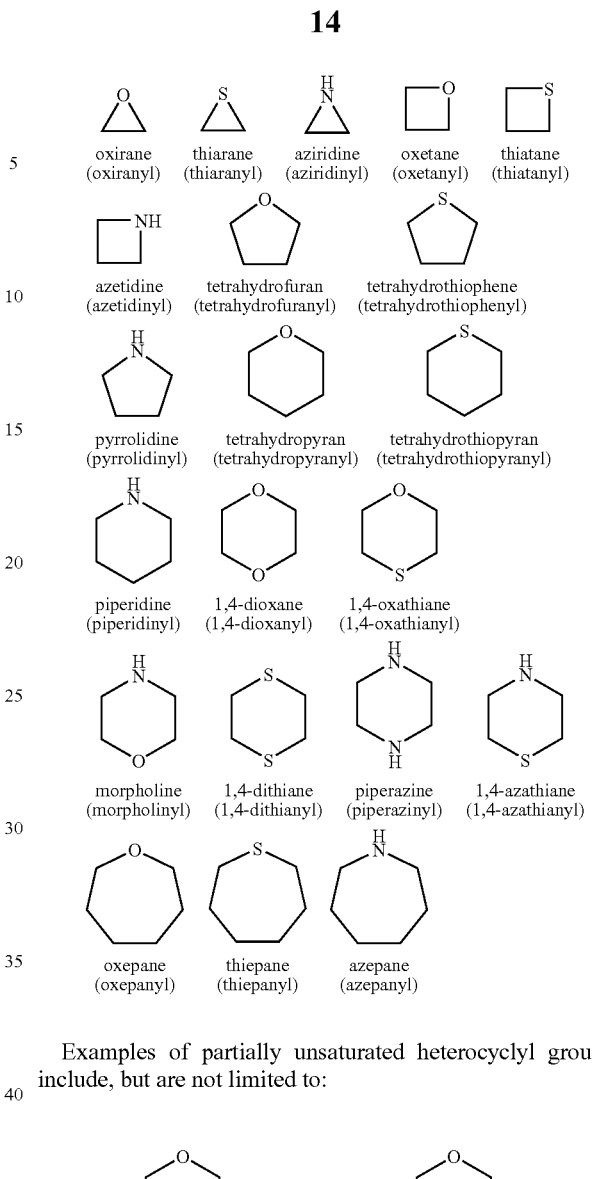

When substituted, each substituted group is preferably one or more selected from halogen, hydroxy, —COR', —COOR', —OCOR", —CONRR', —RNCOR', —NRR', —CN, —NO₂, —CF₃, —SR', —SOR', —SO₂R', —SO₂OR', —SO₂NRR', thiocarbonyl, —RNSO₂R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

A "heteroalicyclic ring" or "heteroalicycle" or "heterocyclic" or "heterocycle" group refers to a monocyclic group having in the ring one or more atoms selected from the group consisting of nitrogen, oxygen and sulfur. The rings may be saturated and also have one or more double bonds (i.e. partially unsaturated). However, the rings may not have a completely conjugated pi-electron system. Preferably, the heteroalicyclic ring contains from 3 to 8 ring atoms. Examples of suitable saturated heteroalicyclic groups include, but are not limited to:

Examples of partially unsaturated heterocyclyl groups include, but are not limited to:

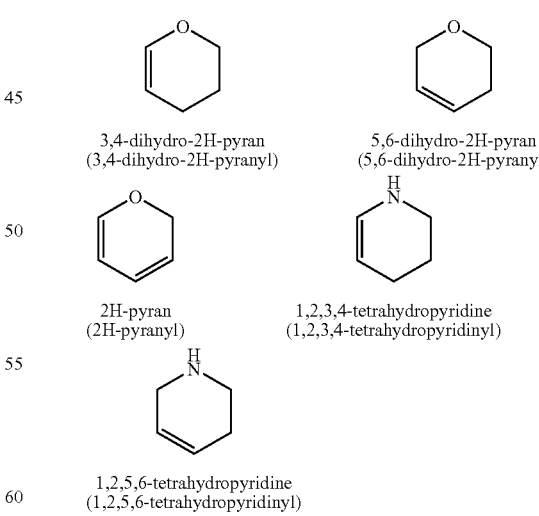

The foregoing groups, as derived from the compounds listed above, may be C-attached or N-attached where such is possible. For instance, a group derived from pyrrole may be pyrrol-1-yl (N-attached) or pyrrol-3-yl (C-attached). The heteroalicyclic ring may be substituted or unsubstituted. The heteroalicyclic ring may contain one or more oxo groups. When substituted, the substituted group(s) is preferably one or more selected halogen, hydroxy, —COR', —COOR', OCOR', —CONRR', —RNCOR', —NRR', —CN, —NO$_2$, —CF$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

A "3-8 Membered heteroalicyclic-(3-8 membered heteroalicyclic)" group refers to a group having two 3-8 membered heteroalicyclic groups covalently bonded to each other through a single ring atom of each. The 3-8 membered heteroalicyclic rings may be any heteroalicyclic ring as defined above. Furthermore, the heteroalicyclic rings may be substituted or unsubstituted as defined above.

"Heterobicyclic" or "heterobicycle" refers to a fused ring (i.e., rings which share an adjacent pair of atoms) group having in the ring(s) one or more atoms selected from the group consisting of nitrogen, oxygen and sulfur and, in addition, having a completely conjugated pi-electron system (i.e.—aromatic heterobicyclic) or one or more double bonds that does not create a completely conjugated pi-electron system, with the proviso that heterobicyclic groups containing highly unstable heteroatom arrangements, such as O—O, O—O—O and the like, are not contemplated by the present invention. One of ordinary skill in the art will recognize unstable groups that are not contemplated by the invention. Preferably, the heterobicyclic group contains from 8-10 ring atoms. The heterobicyclic ring may be substituted or unsubstituted. The heterobicyclic ring may contain one or more oxo groups. Examples of suitable fused ring aromatic heterobicyclic groups include, but are not limited to:

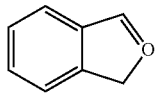
benzofuran
(benzofuranyl)

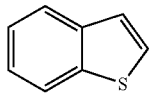
benzothiophene
(benzothiophenyl)

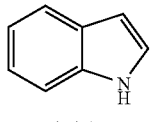
indole
(indolyl)

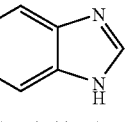
benzimidazole
(benzimidazolyl)

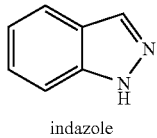
indazole
(indazolyl)

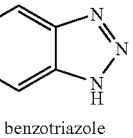
benzotriazole
(benzotriazolyl)

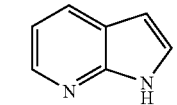
pyrrolo[2,3-b]pyridine
(pyrrolo[2,3-b]pyridinyl)

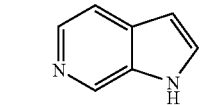
pyrrolo[2,3-c]pyridine
(pyrrolo[2,3-c]pyridinyl)

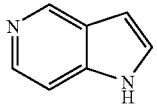
pyrrolo[3,2-c]pyridine
(pyrrolo[3,2-c]pyridinyl)

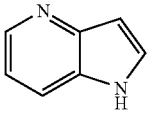
pyrrolo[3,2-b]pyridine
(pyrrolo[3,2-b]pyridinyl)

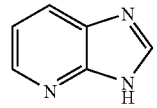
imidazo[4,5-b]pyridine
(imidazo[4,5-b]pyridinyl)

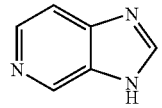
imidazo[4,5-c]pyridine
(imidazo[4,5-c]pyridinyl)

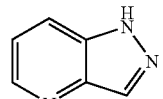
pyrazolo[4,3-d]pyridine
(pyrazolo[4,3-d]pyidinyl)

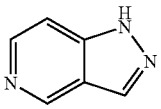
pyrazolo[4,3-c]pyridine
(pyrazolo[4,3-c]pyridinyl)

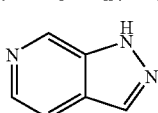
pyrazolo[3,4-c]pyridine
(pyrazolo[3,4-c]pyidinyl)

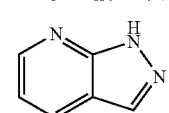
pyrazolo[3,4-b]pyridine
(pyrazolo[3,4-b]pyidinyl)

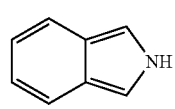
isoindole
(isoindolyl)

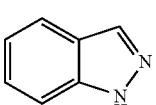
indazole
(indazolyl)

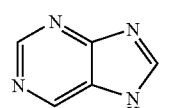
purine
(purinyl)

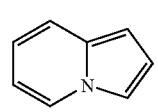
indolizine
(indolininyl)

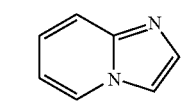
imidazo[1,2-a]pyridine
(imidazol[1,2-a]pyridinyl)

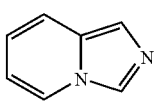
imidazo[1,5-a]pyridine
(imidazol[1,5-a]pyridinyl)

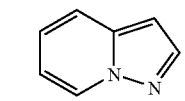
pyrazolo[1,5-a]pyridine
(pyrazolo[1,5-a]pyridinyl)

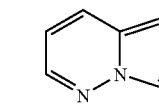
pyrrolo[1,2-b]pyridazine
(pyrrolo[1-2,b]pyridazinyl)

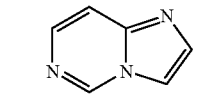
imidazo[1,2-c]pyrimidine
(imidazol[1,2-c]pyrimidinyl)

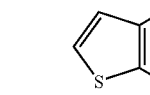
thienopyrimidine
(thienopyrimidinyl)

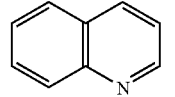
quinoline
(quinolinyl)

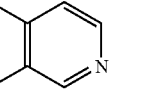
isoquinoline
(isoquinolinyl)

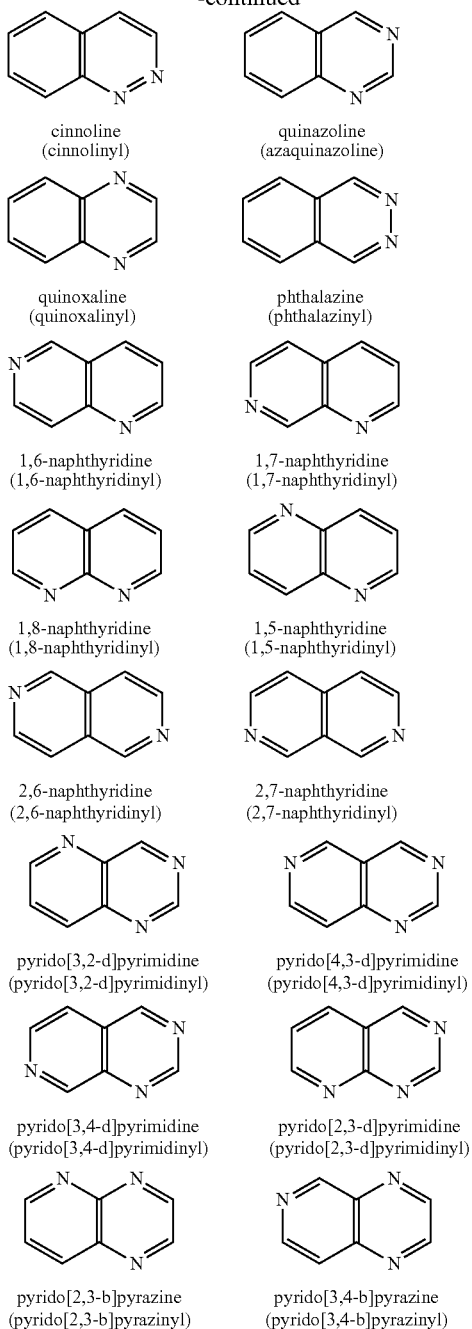

Example of suitable fused ring heterobicyclic groups include, but are not limited to:

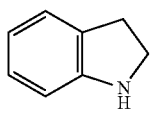 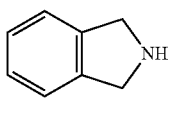

indoline
(indolyl)

isoindoline
(isoindolinyl)

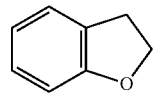 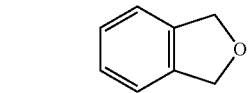

2,3-dihydrobenzofuran
(2,3-dihydrobenzofuranyl)

1,3-dihydrobenzofuran
(1,3-dihydrobenzofuranyl)

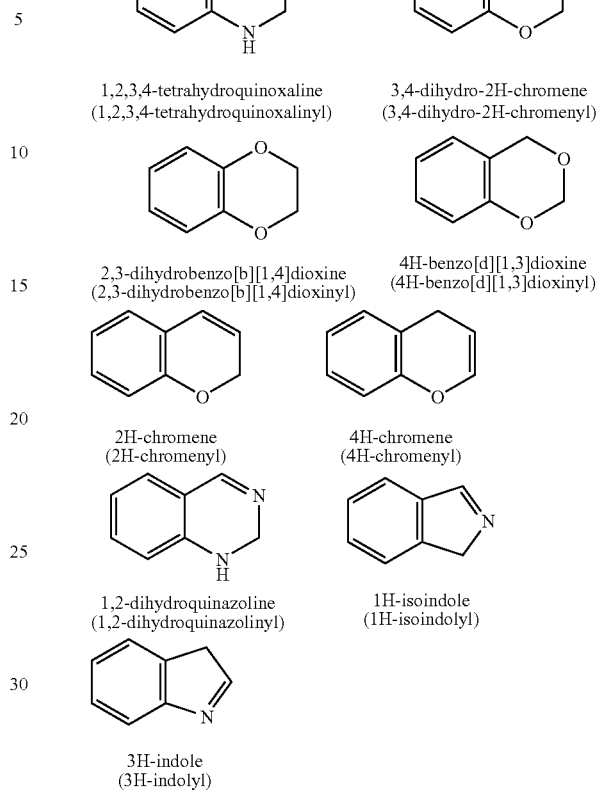

When substituted, the substituted group(s) is preferably one or more selected halogen, hydroxy, —COR', —COOR', OCOR', —CONRR', —RNCOR', —NRR', —CN, —NO$_2$, —CF$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

When used herein, the R groups on substitutents having two or more R groups on different atoms, such as —(CH$_2$)n (NR$^{13}$R$^{14}$)C(O)NR$^{13}$R$^{14}$ or —NR$^{11}$C(O)NR$^{11}$R$^{12}$, may be the same or different. Specifically, in the exemplary substituent —NR$^{11}$C(O)NR$^{11}$R$^{12}$, the two R$^{11}$ groups may be the same or different with respect to each other, likewise, the two R$^{11}$ groups may be the same or different with respect to the R$^{12}$ group. In, for example, —(CH$_2$)$_n$(NR$^{13}$R$^{14}$)C(O) NR$^{13}$R$^{14}$, the two R$^{13}$ groups may be the same or different with respect to each other, and the two R$^{14}$ groups may be the same or different with respect to each other. Likewise, the two R$^{13}$ groups may be the same or different with respect to the two R$^{14}$ group. In addition, where a single atom is substituted by more than one group, the groups on that atom may be the same or different. So, in —NR$^{11}$C(O)NR$^{11}$R$^{12}$, the R$^{11}$ and R$^{12}$ on the same nitrogen may be the same or different from one another.

An "oxo" group refers to a carbonyl moiety such that alkyl substituted by oxo refers to a ketone group.

A "hydroxy" group refers to an —OH group.

An "alkoxy" group refers to both an —O-alkyl and an —O-cycloalkyl group, as defined herein.

An "alkoxycarbonyl" refers to a —C(O)OR.
An "aminocarbonyl" refers to a —C(O)NRR'.
An "aryloxycarbonyl" refers to —C(O)O-aryl.
An "aryloxy" group refers to both an —O-aryl and an —O-heteroaryl group, as defined herein.

An "arylalkyl" group refers to -alkylaryl, where alkyl and aryl are defined herein.

An "arylsulfonyl" group refers to a —SO$_2$aryl.
An "alkylsulfonyl" group refer to a —SO$_2$alkyl.
A "heteroaryloxyl" group refers to a heteroaryl-O group with heteroaryl as defined herein.

A "heteroalicycloxy" group refers to a heteroalicyclic-O group with heteroalicyclic as defined herein.

A "carbonyl" group refers to a —C(=O)R.
An "aldehyde" group refers to a carbonyl group where R is hydrogen.

A "thiocarbonyl" group refers to a —C(=S)—R group.
A "trihalomethanecarbonyl" group refers to a X$_3$CC(O) group, where X is halogen.

A "C-carboxyl" group refers to a —C(O)OR groups.
An "O-carboxyl" group refers to a RC(O)O group.
A "carboxylic acid" group refers to a C-carboxyl group in which R is hydrogen.

A "halo" or "halogen" group refers to fluorine, chlorine, bromine or iodine.

A "trihalomethyl" group refers to a —CX$_3$ group.
A "trihalomethanesulfonyl" group refers to a X$_3$CS(O)$_2$ group.

A "trihalomethanesulfonamido" group refers to a X$_3$CS(O)$_2$NR-group.

A "sulfinyl" group refers to a —S(O)R group.
A "sulfonyl" group refers to a —S(O)$_2$R group.
An "S-sulfonamido" group refers to a —S(O)$_2$NR-group.
An "N-Sulfonamido" group refers to a —NR—S(O)$_2$R group.

An "O-carbamyl" group refers to a —OC(O)NRR' group.
An "N-carbamyl" group refers to a ROC(O)NR-group.
An "O-thiocarbamyl" group refers to a —OC(S)NRR' group.

An "N-thiocarbamyl" group refers to a ROC(S)NR' group.
An "amino" group refers to an —NH$_2$ or an —NRR' group.
A "C-amido" group refers to a —C(O)NRR' group.
An "N-amido" group refers to a R'C(O)NR group.
A "nitro" group refers to a —NO$_2$ group.
A "cyano" group refers to a —CN group.
A "silyl" group refers to a —Si(R)$_3$ group.
A "phosphonyl" group refers to a —P(=O)(OR)$_2$ group.
An "aminoalkyl" group refers to an -alkylNRR' group.
An "alkylaminoalkyl" group refers to an -alkyl-NR-alkyl group.

A "dialkylaminoalkyl" group refers to an -alkylN-(alkyl)$_2$ group.

A "perfluoroalkyl group" refers to an alkyl group where all of the hydrogen atoms have been replaced with fluorine atoms.

Compounds that have the same molecular formula but differ in the nature or sequence of bonding of their atoms or arrangements of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". The chemical formulae referred to herein may exhibit the phenomenon of tautomerism and structural isomerism. This invention encompasses any tautomeric or structural isomeric form and mixtures thereof which possess the ability to modulate c-Met activity and is not limited to any one tautomeric or structural isomeric form.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992). Thus, this invention also encompasses any stereoisomeric form, their corresponding enantiomers (d- and l- or (+) and (−) isomers) and diastereomers thereof, and mixtures thereof, which possess the ability to modulate c-Met activity and is not limited to any one stereoisomeric form.

The compounds of the Formula I or Formula II may exhibit the phenomena of tautomerism and structural isomerism. For example, the compounds described herein may adopt an E or a Z configuration about a double bond or they may be a mixture of E and Z. This invention encompasses any tautomeric or structural isomeric form and mixtures thereof which possess the ability to modulate c-Met activity and is not limited to any one tautomeric or structural isomeric form.

It is contemplated that compounds of the Formula I or Formula II would be metabolized by enzymes in the body of the organism such as human being to generate a metabolite that can modulate the activity of c-Met. Such metabolites are within the scope of the present invention.

Those compounds of the Formula I or Formula II that are acidic in nature are capable of forming base salts with various pharmacologically acceptable cations. Examples of such salts include the alkali metal or alkaline earth metal salts and particularly, the sodium and potassium salts.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of Formula I or Formula II may also exist as tautomers. This invention relates to the use of all such tautomers and mixtures thereof.

This invention also encompasses pharmaceutical compositions containing and methods of treating proliferative disorders or abnormal cell growth through administering prodrugs of compounds of the Formula I or Formula II. Compounds of Formula I or Formula II having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of Formula I or Formula II. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy) methyl and (acyloxy) ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Utilities

The compounds of the invention find use in a variety of applications. As will be appreciated by those skilled in the art, the kinase activity of MET may be modulated in a variety of ways; that is, one can affect the phosphorylation/activation of MET either by modulating the initial phosphorylation of the protein or by modulating the autophosphorylation of the other active sites of the protein. Alternatively, the kinase activity of MET may be modulated by affecting the binding of a substrate of MET phosphorylation.

The compounds of the invention are useful to bind to and/or modulate the activity of a receptor tyrosine kinase. In an embodiment, the receptor tyrosine kinase is a member of the MET subfamily. In a further embodiment, the MET is human MET, although the activity of receptor tyrosine kinases from other organisms may also be modulated by the compounds of the present invention. In this context, modulate means either increasing or decreasing kinase activity of MET. In an embodiment, the compounds of the instant invention inhibit the kinase activity of MET.

The compounds of the invention are used to treat or prevent cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. Thus, in one embodiment, the invention herein includes application to cells or individuals which are afflicted or may eventually become afflicted with any one of these disorders or states.

The compounds, compositions and methods provided herein are particularly deemed useful for the treatment and prevention of cancer including solid tumors such as skin, breast, brain, cervical carcinomas, testicular carcinomas, etc. In an embodiment, the instant compounds are useful for treating cancer. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions. In another embodiment, the compounds of the instant invention are useful for treating or preventing cancer selected from: histiocytic lymphoma, lung adenocarcinoma, small cell lung cancers, pancreatic cancer, liver cancer, gastric cancer, colon cancer, multiple myeloma, glioblastomas and breast carcinoma, In still another embodiment, the compounds of the instant invention are useful for treating cancer selected from: histiocytic lymphoma, lung adenocarcinoma, small cell lung cancers, pancreatic cancer, liver cancer, gastric cancer, colon cancer, multiple myeloma, glioblastomas and breast carcinoma. In another embodiment, the compounds of the instant invention are useful for the prevention or modulation of the metastases of cancer cells and cancer. In particular, the compounds of the instant invention are useful to prevent or modulate the metastases of ovarian cancer, childhood hepatocellular carcinoma, metastatic head and neck squamous cell carcinomas, gastric cancers, breast cancer, colorectal cancer, cervical cancer, lung cancer, nasopharyngeal cancer, pancreatic cancer, glioblastoma and sarcomas.

The compounds of this invention may be administered to mammals, preferably humans, either alone or in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I or Formula II may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I or Formula II are employed. (For purposes of this application, topical application shall include mouth washes and gargles).

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol. When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The instant compounds are also useful in combination with known therapeutic agents and anticancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HTV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY1 17081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-k1]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino] ethyl]-5-[4-hydrooxy-3,5-dimethoxyphenyl]-5,5a,6,8,8a,9-hexohydrofuro(3',4':6,7)naphtho(2,3-d)-1,3-dioxo1-6-one, 2,3-(methylenedioxy)-5-methyl-7-hydroxy-8-methoxy-benzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678 and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kifl4, inhibitors of Mphosphl and inhibitors of Rab6-KIFL.

Examples of "histone deacetylase inhibitors" include, but are not limited to, SAHA, TSA, oxamflatin, PXD101, MG98, valproic acid and scriptaid. Further reference to other histone deacetylase inhibitors may be found in the following manuscript; Miller, T. A. et al. *J. Med. Chem.* 46(24): 5097-5116 (2003).

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylaminol-L-glycero-B-L-manno-heptopyranosyllJadenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-4-oxa-1,11-diazatetracyclo(7.4.1.0.0)-tetradeca-2, 4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp.1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-$\alpha$, interleukin-12, pentosan polysulfate, cyclooxygenase inhibitors, including nonsteroidal antiinflammatories (NSAIDs) like aspirin and ibuprofen as well as selective cyclooxygenase-2 inhibitors like celecoxib and rofecoxib (*PNAS*, Vol. 89, p. 7384 (1992); *JNCI*, Vol. 69, p. 475 (1982); *Arch. OpthalmoL*, Vol. 108, p.573 (1990); *Anat. Rec*, Vol. 238, p. 68 (1994); *FEBS Letters*, Vol. 372, p. 83 (1995); *Clin. Orthop.* Vol. 313, p. 76 (1995); *J. Mol. Endocrinol*, Vol. 16, p. 107 (1996); *Jpn. J. Pharmacol*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal antiinflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of EGFR (for example gefitinib and erlotinib), inhibitors of ERB-2 (for example trastuzumab), inhibitors of IGFR, inhibitors of cytokine receptors, inhibitors of MET, inhibitors of PBK (for example LY294002), serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)-phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integral blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-k1]pyrrolo

[3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD 121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol Vis. Sci.* 2000; 41:2309-2317). More recently, PPAR-δ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet* 61:785-789, 1997) and Kufe et al (*Cancer Medicine*, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8): 1105-13), and interferon gamma (*J Immunol* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other antiemetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds. Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0428 434, 0429 366, 0430 771, 0436 334, 0443 132, 0 482 539, 0 498 069, 0 499 313, 0 512 901, 0512 902, 0 514273, 0514274, 0 514275, 0514276, 0515 681, 0517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610793, 0 634 402, 0 686 629, 0 693 489, 0 694 535, 0 699 655, 0 699 674, 0 707 006, 0 708 101, 0 709 375, 0709 376, 0 714 891, 0 723 959, 0 733 632 and 0776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2293 169, and 2 302 689. The preparation of such compounds is described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

Thus, the scope of the instant invention encompasses the use of the instantly claimed compounds in combination with a second compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HTV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an apoptosis inducing agent, a bisphosphonate, an aromatase inhibitor, an siRNA therapeutic and an agent that interferes with a cell cycle checkpoint.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-a, interleukin-12, pentosan polysulfate, a cyclooxygenase inhibitor, carboxyamidotriazole, combretastatin A-4, squalamine, 6-0-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I or Formula II in combination with radiation therapy and/or in combination with a compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HTV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an apoptosis inducing agent, a bisphosphonate, an aromatase inhibitor, an siRNA therapeutic and an agent that interferes with a cell cycle checkpoint.

And yet another embodiment of the invention is a method of treating cancer that comprises administering a therapeutically effective amount of a compound of Formula I or Formula II in combination with paclitaxel or trastuzumab. The invention further encompasses a method of treating or preventing cancer that comprises administering a therapeutically effective amount of a compound of Formula I or Formula II in combination with a COX-2 inhibitor.

The instant invention also includes a pharmaceutical composition useful for treating or preventing cancer that comprises a therapeutically effective amount of a compound of Formula I or Formula II and a compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HTV protease inhibitor, a reverse transcriptase inhibitor, an angiogenesis inhibitor, a PPAR-γ agonist, a PPAR-δ agonist; an inhibitor of cell proliferation and survival signaling, a bisphosphonate, an aromatase inhibitor, an siRNA therapeutic and an agent that interferes with a cell cycle checkpoint.

These and other aspects of the invention will be apparent from the teachings contained herein.

General Reaction Schemes

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of Formula I or Formula II hereinabove.

One of skill in the art will recognize that this general scheme may be modified and yet still produce the compounds of the present invention. As shown in Scheme 1, reaction of a suitably substituted 2,4-dichloropyrimidin-5-amine III with a proper amine IV under both acidic conditions (*Chem. Pharm. Bull.* 1987, 35 (12), 4972-4976) and basic conditions provides 2-chloropyrimidine-4,5-diamine V. 5-Chloro-3H-[1,2,3]triazolo[4,5-d]pyrimidine VI can be prepared by cyclizing an intermediate of 2-chloropyrimidine-4,5-diamine V in the presence of a nitrite salt, such as $NaNO_2$, a suitable acid, e.g. hydrochloric acid, and/or acetic acid and the like, and alternatively in the presence of isoamyl nitrite in a suitable solvents under heating. Treatment of 5-chloro-3H-[1,2,3]triazolo[4,5-d]pyrimidine VI with $NH_3$ in a suitable solvent, such as ethanol, affords 3H-[1,2,3]triazolo[4,5-d]pyrimidin-5-amine VII. The amino group at the 5-position on the 3H-[1,2,3]triazolo[4,5-d]pyrimidine VII can be converted into iodide or bromine by treatment with isoamyl nitrite in diiodomethane or tribromomethane (*Chem. Pharm. Bull.* 1991, 39 (11), 3037-3040) to provide 5-iodo or bromo-3H-[1,2,3]triazolo[4,5-d]pyrimidine VIII. A transition-metal catalyzed cross-coupling reaction of 5-chloro-3H-[1,2,3]triazolo[4,5-d]pyrimidine VI or 5-iodo or bromo-3H-[1,2,3]triazolo[4,5-d]pyrimidine VIII with an appropriately substituted boronic acid, boronate ester, zincate or stannane $R^1Y$ under Suzuki (Miyaura, N., Suzuki, A., *Chem. Rev.* 1995, 95, 2457), Negishi (*J. Org. Chem.* 1977, 42, 1821), or Stille conditions (*Agnew. Chem., Int. Ed. Engl.* 1986, 25, 508 and references therein) provides the coupling product, 5-substituted-3H-[1,2,3]triazolo[4,5-d]pyrimidine I and II.

SCHEME 1

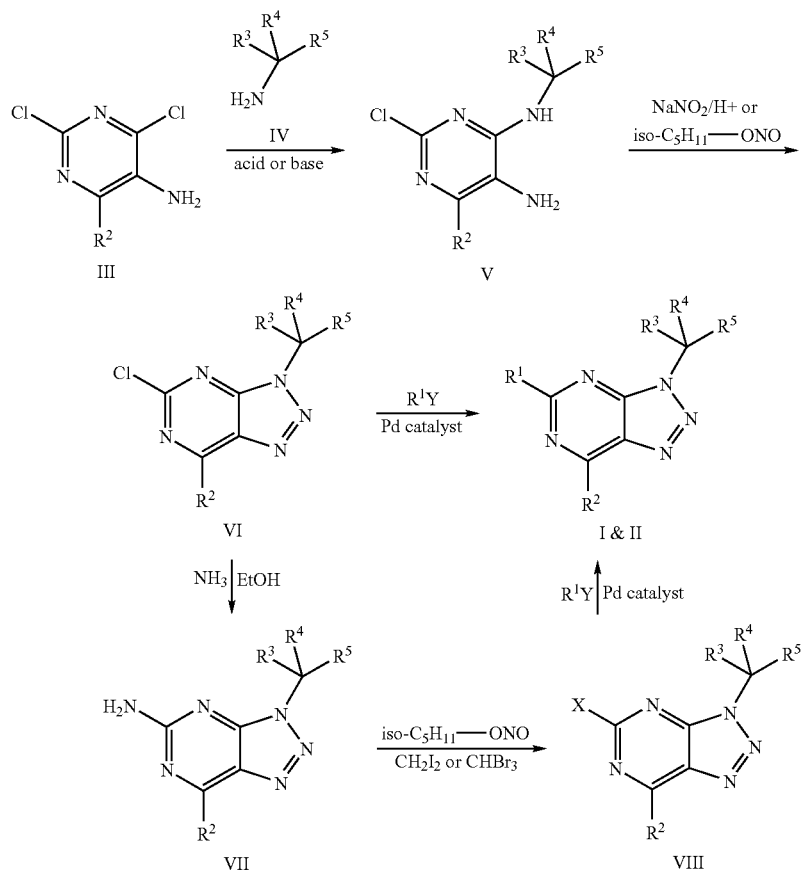

Scheme 2 illustrates an alternative route to prepare an intermediate 2-chloropyrimidine-4,5-diamine V. 2,4-Dichloro-5-nitropyrimidine IX reacts with a suitable amine IV in the presence of N-diisopropylethanamine to provide an intermediate X. Reduction of an intermediate X in the presence of $H_2$, a suitable catalyst such as Platina or Palladium on charcoal, a suitable catalyst poison, such as a thiophene solution, and a suitable solvent, such as methanol affords an intermediate 2-chloropyrimidine-4,5-diamine V. Alternatively, the reduction can be performed in the presence of Fe and an ammonium chloride solution, or in the presence of $SnCl_2$ and an alcohol solution to provide the same intermediate V.

SCHEME 2

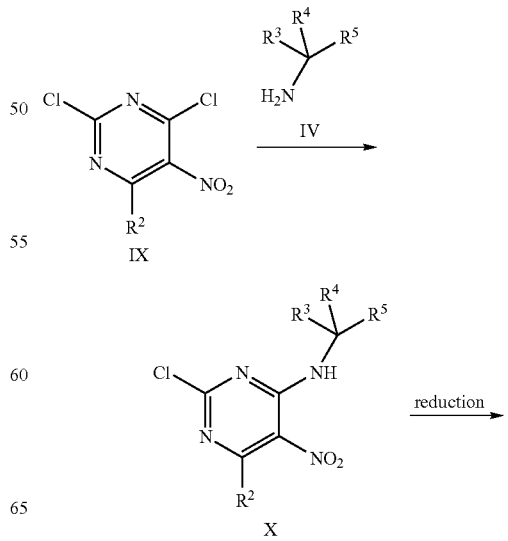

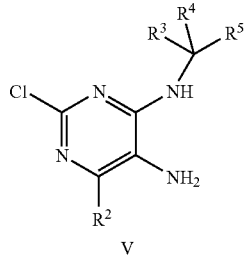

V

Scheme 3 further illustrates that diversified modification of 5-chloro-3H-[1,2,3]triazolo[4,5-d]pyrimidine VI with O-, N-, and S-nucleophiles (*Chem. Pharm. Bull.* 1989, 37(7), 1731-1734) can provide diversified 5-substituted 3H-[1,2,3]triazolo[4,5-d]pyrimidine XI, XII and XIII.

SCHEME 3

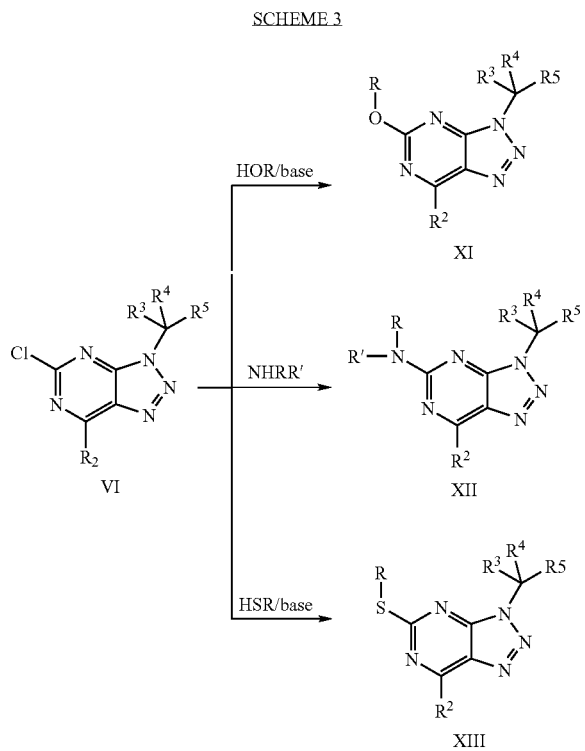

EXAMPLES

Certain abbreviations, used in the Examples, are defined below:
APCI: Atmospheric pressure chemical ionization
LCMS: Liquid chromatographic mass spectrometry
DMF: N,N-dimethylformamide
HPLC: High-performance liquid chromatography (also known as high-pressure liquid chromatography)
AcOH: Acetic acid
Pd(dppf).CH$_2$Cl$_2$: [1,1'-Bis(diphenylphosphino)ferrocene] dichloropalladium(II) complex with CH$_2$Cl$_2$
DME: Dimethyl ether
EtOAc: Ethyl acetate
MeOH: Methanol
EtOH: Ethanol
DMSO: Dimethylsulfoxide
DIPEA: Diisopropylethylamine
AUC$_{(0-t)}$: Area under the curve from the time of dosing to the time of the last observation
AUC$_{(0-\infty)}$: Area under the curve from the time of dosing to infinity
C$_{max}$: Maximum concentration
SD: Standard deviation
T$_{max}$: Time of the maximum concentration
T$_{1/2}$: Terminal half-life Examples provided are intended to assist in a further understanding of the invention. Particular materials employed, species and conditions are intended to be illustrative of the invention and not limiting of the reasonable scope thereof.

Example 1

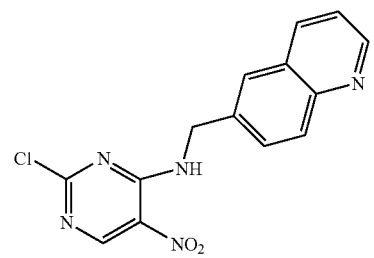 [SMILES: O=[N+]([O-])c1cnc(Cl)nc1NCc1ccc2ncccc2c1]

Step 1: 2-Chloro-5-nitro-N-(quinolin-6-ylmethyl)pyrimidin-4-amine. To a solution of 2,4-dichloro-5-nitro-pyrimidine (2.80 g, 14.4 mmol) in dioxane (20 mL) was added dropwise a solution of quinolin-6-ylmethanamine (2.28 g, 14.4 mmol) in dioxane (4 mL) and DIPEA (2.56 mL, 14.7 mmol). The reaction mixture was stirred at room temperature for 2 hours. Dichloromethane (20 mL) was then added to the reaction mixture. The solvent was removed in vacuo and the crude product was purified by flash chromatography over silica gel, using 50% EtOAc-hexane, gave the desired product (3.18 g, 70%) as a pale yellow solid. LCMS (APCI) m/z 316.0 (M+H$^+$).

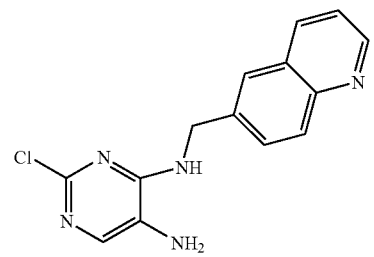

Step 2: 2-Chloro-N$^4$-(quinolin-6-ylmethyl)pyrimidine-4,5-diamine

A suspension of 2-chloro-5-nitro-N-(quinolin-6-ylmethyl) pyrimidin-4-amine (2.25 g, 7.14 mmol), SnCl$_2$ (7.18 g, 32 mmol) in ethanol (50 mL) and CHCl$_3$ (10 mL) was refluxed for 5 h. The mixture was allowed to cool to room temperature and the solvent was evaporated. The residue was basified to pH 10 by saturated aqueous NaHCO$_3$. The resulting suspension was stirred in ethanol (500 mL) for 2 h and filtered through a pad of silica gel. The filtrate was evaporated. Flash chromatography of the residue over silica gel, using 100%

EtOAc to 10% MeOH-EtOAc with 0.5% NH₃H₂O, gave the desired product (1.02 g, 50%) as a white solid. ¹H NMR (300 MHz, CD₃OD) δ 4.88 (s, 2H), 7.46-7.53 (m, 2H), 7.77-8.02 (m, 3H), 8.32 (d, 1H, J=8.0 Hz), 8.8 (m, 1H); LCMS (APCI) m/z 286.2 (M+H⁺).

Alternative synthesis of 2-chloro-N⁴-(quinolin-6-ylmethyl)pyrimidine-4,5-diamine: A mixture of quinolin-6-ylmethanamine (193 mg, 1.22 mmol), 2,4-dichloropyrimidin-5-amine (200 mg, 1.22 mmol) and DIPEA (0.64 mL, 3.66 mmol) in n-butanol (2 mL) was heated in the microwave at 200° C. for 1 h. After cooling to room temperature, dichloromethane (2 mL) was added to the mixture. Flash chromatography of the resulting mixture over silica gel, using 100% EtOAc to 10% MeOH-EtOAc with 0.5% NH₃H₂O, gave the desired product (142 mg, 40%) as a white solid. LCMS (APCI) m/z 286.2 (M+H⁺).

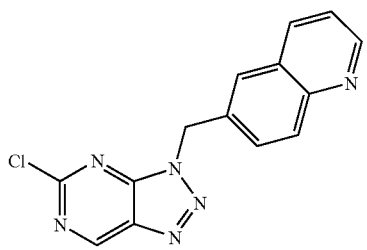 [SMILES: Clc1ncc2nnn(Cc3ccc4ncccc4c3)c2n1]

Step 3: 6-45-Chloro-3H-[1,2,3]triazolo[4,5-d]pyrimidin-3-yl)methyl)quinoline

To a solution of 2-chloro-N⁴-(quinolin-6-ylmethyl)pyrimidine-4,5-diamine (1.02 g, 3.58 mmol) in DMF (12 mL) was added dropwise isoamyl nitrite (0.58 mL, 4.30 mmol) at room temperature. The reaction mixture was then heated at 50° C. for 2 h, cooled and quenched with saturated solution of Na₂SO₃ (10 mL). Water (20 mL) was added to dissolve the precipitate, followed by EtOAc (60 mL). The organic layer was separated and the aqueous layer was extracted with EtOAc (4×60 mL). The combined organic extracts were washed with saturated solution of NaHCO₃ and brine, dried over Na₂SO₄. The solvent was evaporated and the resulting residue was dried under high vacuum to give the desired product (0.72 g, 68%). ¹H NMR (300 MHz, CDCl₃) δ 6.04 (s, 2H), 7.40-8.17 (m, 5H), 8.94 (m, 1H), 9.42 (s, 1H); LCMS (APCI) m/z 297.0 (M+H⁺).

Example 2

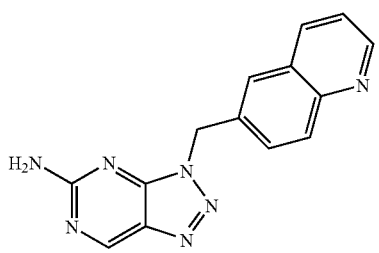 [SMILES: Nc1ncc2nnn(Cc3ccc4ncccc4c3)c2n1]

3-(Quinolin-6-ylmethyl)-3H-[1,2,3]triazolo[4,5-d]pyrimidin-5-amine

A suspension of 6-((5-chloro-3H-[1,2,3]triazolo[4,5-d]pyrimidin-3-yl)methyl)quinoline (134 mg, 0.453 mmol) in NH₃ saturated EtOH (3 mL) was heated at 120° C. in a sealed pressure tube for 2.5 h. After cooling to room temperature, EtOH (20 mL) was added to the reaction mixture. The precipitate was collected by filtration and dried to afford the desired product (112 mg, 90%). ¹H NMR (300 MHz, DMSO-d₆) δ 5.87 (s, 2H), 7.39 (br s, 2H), 7.51-8.04 (m, 4H), 8.34 (m, 1H), 8.89 (m, 1H), 9.21 (s, 1H); LCMS (APCI) m/z 278.2 (M+H⁺).

Example 3

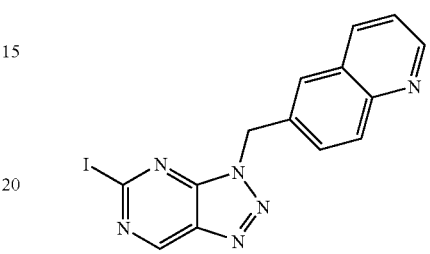

6-((5-Iodo-3H-[1,2,3]triazolo[4,5-d]pyrimidin-3-yl)methyl)quinoline. Isoamyl nitrite (0.78 mL) was added to a suspension of 3-(quinolin-6-ylmethyl)-3H-[1,2,3]triazolo[4,5-d]pyrimidin-5-amine (102 mg, 0.370 mmol) in CH₂I₂ (2.4 mL) under a nitrogen atmosphere. The mixture was stirred at 85° C. for 1 h. The solvent was removed under reduced pressure. Flash chromatography of the resulting residue over silica gel to afford the desired product (57 mg, 40%). ¹H NMR (300 MHz, CDCl₃) δ 6.03 (s, 2H), 7.44 (m, 1H), 7.79-8.18 (m, 4H), 8.94 (m, 1H), 9.27 (s, 1H); LCMS (APCI) m/z 389.0 (M+H⁺).

Example 4

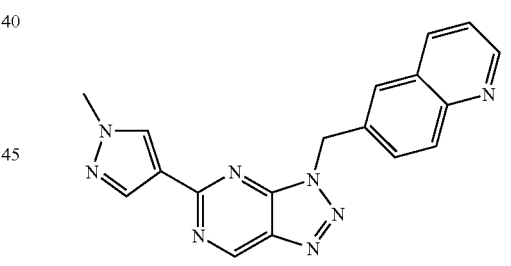

6-((5-(1-Methyl-1H-pyrazol-4-yl)-3H-[1,2,3]triazolo[4,5-d]pyrimidin-3-yl)methyl)quinoline To a solution of 6-((5-chloro-3H-[1,2,3]triazolo[4,5-d]pyrimidin-3-yl)methyl)quinoline (393 mg, 1.33 mmol) in DME (8 mL) was added 1-methyl-4-(4,4,5,5-tetramethyl-1,3,2-dioxaborolan-2-yl)-1H-pyrazole (415 mg, 1.99 mmol) and Cs₂CO₃ (1.30 g, 3.98 mmol) in H₂O (1.3 mL). The reaction mixture was degassed twice. The palladium catalyst Pd(dppf).CH₂Cl₂ (63 mg, 0.077 mmol) was added and the reaction mixture was degassed for two more times, and heated to 80° C. for 15 h under nitrogen. After cooling to room temperature, the solvent was removed under reduced pressure. Flash chromatography of the residue over silica gel, using 50% hexane in EtOAc to 100% EtOAc to 10% MeOH in EtOAc, gave the desired product (130 mg, 29%) as a white solid. ¹H NMR (300 MHz, CDCl₃) δ 4.00 (s, 3H), 6.04 (s, 2H), 7.39-8.29 (m, 7H), 8.92 (m, 1H), 9.44 (s, 1H); LCMS (APCI) m/z 343.0 (M+H⁺).

Example 5

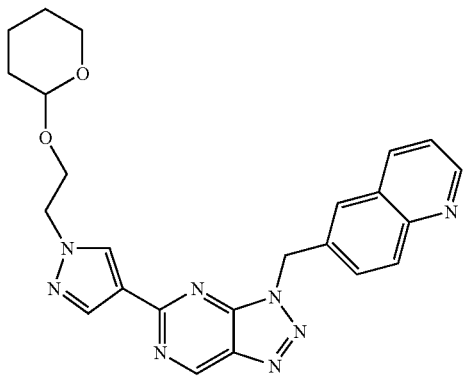 [SMILES: c1cnc2ccc(Cn3nnc4cnc(-c5cnn(CCOC6CCCCO6)c5)nc43)cc2c1]

Step 1: 6-((5-(1-(2-(Tetrahydro-2H-pyran-2-yloxy) ethyl)-1H-pyrazol-4-yl)-3H-[1,2,3]triazolo[4,5-d] pyrimidin-3-yl)methyl)quinoline To a solution of 6-((5-chloro-3H-[1,2,3]triazolo[4,5-d]pyrimidin-3-yl)methyl)quinoline (393 mg, 1.33 mmol) in DME (8 mL) was added 1-(2-(tetrahydro-2H-pyran-2-yloxy) ethyl)-4-(4,4,5,5-tetramethyl-1,3,2-dioxaborolan-2-yl)-1H-pyrazole (642 mg, 1.99 mmol) and Cs₂CO₃ (1.30 g, 3.98 mmol) in H₂O (1.3 mL). The reaction mixture was degassed twice. The palladium catalyst Pd(dppf).CH₂Cl₂ (63 mg, 0.077 mmol) was added and the reaction mixture was degassed for two more times, and heated to 80° C. for 15 h under nitrogen. After cooling to room temperature, the solvent was removed under reduced pressure. Flash chromatography of the residue over silica gel, using 50% hexane in EtOAc to 100% EtOAc to 10% MeOH in EtOAc, gave the desired product (237 mg, 39%). ¹H NMR (300 MHz, CDCl₃) δ 1.23-1.82 (m, 6H), 3.42-4.59 (m, 7H), 6.04 (s, 2H), 7.41 (m, 1H), 7.82-7.85 (m, 1H), 7.90 (m, 1H), 8.08-8.15 (m, 2H), 8.31 (s, 1H), 8.34 (s, 1H), 8.90-8.92 (m, 1H), 9.46 (s, 1H); LCMS (APCI) m/z 457.2 (M+H⁺).

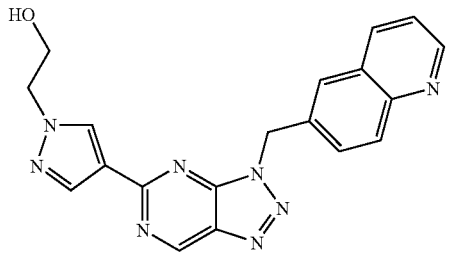 [SMILES: OCCn1cc(-c2ncc3nnn(Cc4ccc5ncccc5c4)c3n2)cn1]

Step 2: 2-(4-(3-(Quinolin-6-ylmethyl)-3H-[1,2,3] triazolo[4,5-d]pyrimidin-5-yl)-1H-pyrazol-1-yl)ethanol A mixture of 6-((5-(1-(2-(tetrahydro-2H-pyran-2-yloxy) ethyl)-1H-pyrazol-4-yl)-3H-[1,2,3]triazolo[4,5-d]pyrimidin-3-yl)methyl)quinoline (237 mg, 0.520 mmol) and TsOH.H₂O (119 mg, 0.624 mmol) in MeOH (15 mL) was stirred for 3 h at room temperature. The solvent was removed under reduced pressure. The crude product was purified by reverse phase HPLC (CH₃CN, H₂O gradient plus 0.1% AcOH) to afford the title compound, after lyophilization, as a white powder (116 mg, 60%). ¹H NMR (300 MHz, DMSO-d₆) δ 3.72 (dd, 2H, J=10.8, 5.4 Hz), 4.18 (t, 2H, J=5.4 Hz), 4.90 (t, 1H, J=5.3 Hz), 6.06 (s, 2H), 7.47 (m, 1H), 7.76 (m, 1H), 7.93-7.97 (m, 2H), 8.12 (m, 1H), 8.31 (m, 1H), 8.45 (s, 1H), 8.90 (m, 1H), 9.64 (s, 1H); LCMS (APCI) m/z 373.2 (M+H⁺).

Biological Assays

In vitro kinase assays may be used to determine the level of activity and effect of the different compounds of the present invention on one or more of the protein kinases (PKs). Similar assays can be designed along the same lines for any PK using techniques well known in the art (see, for example, FEBS Lett. 1991, 292, 69-72).

A general procedure is as follows: compounds and kinase assay reagents are introduced into test wells. The assay is initiated by addition of the kinase enzyme. Enzyme inhibitors reduce the measured activity of the enzyme.

IC₅₀ Determination for the Inhibition of c-Met

The compounds of the instant invention described in the Examples were screened for their ability to inhibit c-Met kinase activity using a standard c-Met kinase screening services (J. Biomol. Screen. 2006, 11, 48-56) provided by Reaction Biology Corporation (One Great Valley Parkway, Suite 8, Malvern, Pa. 19355, USA). The compounds were tested in a 10-dose IC₅₀ with 3-fold serial dilution starting at 3 μM. Reactions were carried out at 10 μM ATP. Assay results in the form of IC₅₀ values (μM) are summarized in Table 1.

TABLE 1

| Compounds | Examples | c-Met IC₅₀ (μM) |
|---|---|---|
| (structure) | 1 | 0.167 |
| (structure) | 2 | 0.040 |

TABLE 1-continued

| Compounds | Examples | c-Met IC$_{50}$ (µM) |
|---|---|---|
| 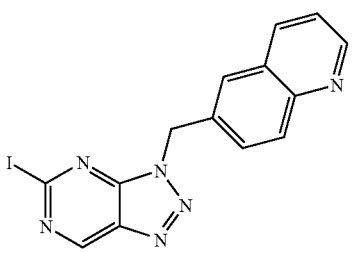 [SMILES: Ic1ncc2nnn(Cc3ccc4ncccc4c3)c2n1] | 3 | 0.079 |
| 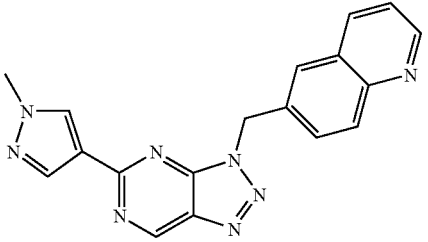 [SMILES: Cn1cc(-c2ncc3nnn(Cc4ccc5ncccc5c4)c3n2)cn1] | 4 | 0.024 |
| 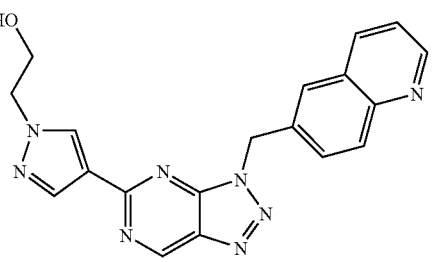 | 5 | 0.009 |

In Vivo Pharmacokinetics Study

The compounds of the present invention were formulated as a solution in a 30:70 (PEG 400:acidified H$_2$O) vehicle. This solution was administered orally (p.o.) at 10 mg/kg and intravenously (i.v.) at 2.5 mg/kg to two distinct groups (n=3) of male Sprague Dawley rats (body weight of 220-250 g). The animals used in the oral dosing group were fasted for 12 hrs before the drug administration. The blood samples were collected via retro-orbital puncture at 0 hour (pre-dose), 0.083, 0.25, 0.5, 1, 2, 4, 6, 8, and 24 hours post-dose. The blood plasma was isolated and HPLC was performed to determine the concentration of the test compounds in blood plasma. Standard set of pharmacokinetic parameters including Area Under the Curves (AUC's), elimination half-lives and bioavailabilities etc. were calculated using FDA certified pharmacokinetic program WinNonlin Professional v5.2 (Pharsight, USA).

The bioavailability was calculated as F (%)=(Dose$_{iv}$×AUC$_{oral(0-\infty)}$)/(Dose$_{oral}$×AUC$_{iv(0-\infty)}$)100%. The plasma concentration-time curve of example 5 in male rats following intravenous and oral administration was shown in FIG. 1. Selected pharmacokinetics parameters of example 5 in male rats following intravenous and oral administration were listed in Table 2.

TABLE 2

| | AUC$_{(0-t)}$ µg/L hr | AUC$_{(0-\infty)}$ µg/L hr | t$_{1/2}$ hr | T$_{max}$ hr | C$_{max}$ µg/L | F % |
|---|---|---|---|---|---|---|
| IV (2.5 mg/kg) | | | | | | |
| R 1 | 5472.46 | 5479.91 | 2.62 | 0.08 | 2698.38 | |
| R 2 | 3451.75 | 3741.58 | 2.59 | 0.08 | 2417.88 | |
| R 3 | 7274.77 | 7310.08 | 3.23 | 0.08 | 3019.57 | |
| mean | 5399.66 | 5510.52 | 2.81 | 0.08 | 2711.94 | |
| SD | 1912.55 | 1784.45 | 0.37 | 0.00 | 301.07 | |
| PO (10 mg/kg) | | | | | | |
| R 4 | 17444.81 | 17494.94 | 2.88 | 2.00 | 2539.64 | 79.37 |
| R 5 | 15454.20 | 15509.49 | 2.82 | 2.00 | 1505.63 | 70.36 |
| R 6 | 15954.84 | 16010.05 | 2.98 | 2.00 | 2299.65 | 72.63 |
| mean | 16284.62 | 16338.16 | 2.89 | 2.00 | 2114.97 | 74.12 |
| SD | 1035.47 | 1032.59 | 0.08 | 0.00 | 541.18 | 4.68 |

U87MG Glioblastoma Tumour Xenograft Model

Introduction

The U87MG glioblastoma cell line (obtained from Institute of Biochemistry and Cell Biology, Shanghai Institutes for Biological Sciences) expresses the c-Met receptor and responds to Human Growth Factor (HGF). This study investigated whether treatment with an inhibitor of c-Met is efficacious against the U87MG glioblastoma tumor xenograft model. The study utilized a tumor growth inhibition (TGI) assay to test per os (p.o.) compound monotherapy in groups of eight nude mice. A control group was treated with a 30:70 (PEG 400:acidified H$_2$O) vehicle. All treatments began on Day 1 (D1) in mice bearing established subcutaneous (s.c.) U87MG tumors.

Method and Materials

Mice:

Female athymic nude mice (BALB/cA, Shanghai Laboratories Animal Center, Shanghai, China) were 7-8 weeks old with a body weight range of 19-21 g at the beginning of the study. Food and water were available ad libitum throughout the study. Mice were housed in SPF (Specific Pathogen Free) area of Medicilon/MPI animal facility. Environmental control for the animal room was set to maintain a temperature of 18-25° C., humidity of 30-70%, and a 12-hour light/12-hour dark cycle. Animals had previously been acclimated to study procedures prior to initial dose administration. Animals to be used on test were selected based on overall health and acclimation to caging. This study was conducted in accordance with Guide for the Care and Use of Laboratory Animals (Natural Academy Press, Washington, D.C., 1996) and Medicilon/MPI Preclinical Research (Shanghai) LLC Standard Operating Procedures.

Tumor Implantation:

U-87 MG human glioblastoma cells were purchased from Institute of Biochemistry and Cell Biology, Shanghai Institutes for Biological Sciences. The cells were maintained in vitro Eagle's Minimum Essential Medium supplemented with 10% heat inactivated fetal calf serum. Cells were cultured at 37° C. in an atmosphere of 5% CO$_2$ in air and routinely sub-cultured twice weekly by trypsin-EDTA treatment. Cells in an exponential growth phase were harvested and counted for tumor inoculation. Each test mouse was subcutaneously inoculated with 1×10$^7$ U87-MG tumor cells in 0.1 ml medium at the right flank of the mouse for tumor model development. During the experiment, the implanted tumors were measured by external caliper every other day in a blind fashion. Nine days later, on Day 1 of the study, mice with well-established tumors (about 150 mm$^3$) were randomly assigned into 4 groups (n=8 mice/group). Tumor volume was calculated using the formula:

Tumor Volume=$w^2 \times l/2$ where w=width and l=length in mm of the tumor. Tumor weight may be estimated with the assumption that 1 mg is equivalent to 1 mm$^3$ of tumor volume.

Drug Treatment:

Dosing solutions of the compound, example 5 of the present invention were prepared fresh weekly in a vehicle consisting of 30:70 (PEG 400:acidified H$_2$O) solution. In all groups, the dosing volume of 0.2 mL/20 g mouse was scaled to the body weight of each animal Tumor Growth Inhibition (TGI) Analysis:

TGI was calculated from the difference between the median tumor growth volumes of vehicle-treated and drug-treated mice, expressed as a percentage of the median tumor growth volume of the vehicle-treated control group, by the following relation:

%TGI=100×(Median Tumor Growth Volume$_{control}$−Median Tumor Growth Volume$_{drug-treated}$)//Median Tumor Growth Volume$_{control}$ The MTV (n) is defined as the median tumor volume (MTV) for the number of animals, n, remaining in the study on that day. The Median Tumor Growth Volume=Median Tumor Volume−Median Tumor Volume$_{initial}$.

Toxicity:

Animals were weighed daily for the first five days after the drug treatment and then every other day throughout the study. The mice were examined frequently for overt signs of any adverse, drug-related side effects, and clinical signs of toxicity were recorded when observed. Throughout this study no adverse effects on the mouse body weight and clinical signs of toxicity were noted.

Results and Graphical Analyses:

Tumor growth was plotted as the median tumor volume, versus time, for each group in the study. The differences in the tumor size between the treatment groups and the vehicle group are analyzed for significance using the unpaired two-tailed Student's t-test. P<0.05 is considered to be statistically significant. Results of the U87MG tumor growth study are shown in FIG. 2.

FIG. 2:

Compound of Example 5 was administered orally at doses of 10, 40 mg/kg once a day (q.d.), and 30 mg/kg twice a day (b.i.d.). All doses produced statistically significant tumor growth inhibition of U87MG tumors grown subcutaneously in athymic nude mice (p<0.05) from Day 6 and the doses of 40 mg/kg (q.d.) and 30 mg/kg (b.i.d.) produced statistically significant tumor growth inhibition (p<0.05) from Day 4 after the drug treatment. On the last day of treatment (Day 12), compared to vehicle treated-controls, tumor growth was inhibited by 58%, 66% and 70% at doses of 10, 40 mg/kg (q.d.), and 30 mg/kg (b.i.d.), respectively.

What is claimed is:

1. A compound of Formula I or partially deuterated Formula I:

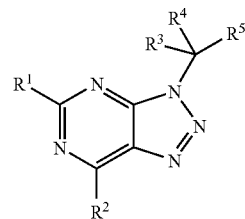

I or a pharmaceutically acceptable salt thereof, wherein
$R^1$ is independently selected from —O(CH$_2$)$_n$OR$^{11}$, —C(O)R$^{11}$, —C(O)OR$^{11}$, —C(O)NR$^{11}$R$^{12}$, C$_3$-C$_8$ cycloalkyl, 3-8 membered heteroalicyclic, 3-8 membered heteroalicyclic-(3-8 membered heteroalicyclic), 8-10 membered heterobicyclic, 5-7 membered heteroaryl, C$_6$-C$_{10}$ aryl, C$_2$-C$_6$ alkenyl, and C$_2$-C$_6$ alkynyl wherein C$_3$-C$_8$ cycloalkyl, 3-8 membered heteroalicyclic, 8-10 membered heterobicyclic, 5-7 membered heteroaryl, C$_6$-C$_{10}$ aryl, C$_2$-C$_6$ alkenyl, and C$_2$-C$_6$ alkynyl are optionally substituted by one or more moieties selected from the group consisting of Br, Cl, F, —(CH$_2$)$_n$CH(OR$^{11}$)CH$_3$, —(CH$_2$)$_n$OR$^{11}$, —(CH$_2$)$_n$C(CH$_3$)$_2$OR$^{11}$, —C(O)R$^{11}$, —C(O)OR$^{11}$, —(CR$^{11}$R$^{12}$)$_n$C(O)OR$^{11}$, —C(O)NR$^{11}$R$^{12}$, —(CR$^{11}$R$^{12}$)$_n$C(O)NR$^{11}$R$^{12}$, —(CH$_2$)$_n$NR$^{11}$R$^{12}$, —S(O)$_2$R$^{11}$, —S(O)R$^{11}$, —S(O)$_2$NR$^{11}$R$^{12}$, —CF$_3$, —(CH$_2$)H, —(CH$_2$)$_n$NR$^{11}$C(O)NR$^{11}$R$^{12}$, —(CH$_2$)$_n$NR$^{11}$C(O)OR$^{12}$, —NR$^{11}$C(O)R$^{12}$, —NR$^{11}$C(O)OR$^{12}$, —NR$^{11}$S(O)$_2$R$^{12}$, —CN, —NO$_2$, oxo, C$_1$-C$_6$ alkyl, C$_3$-C$_8$ cycloalkyl, —(CH$_2$)$_n$(3-8 membered heteroalicyclic), —(CH$_2$)$_n$(5-7 membered heteroaryl), —(CH$_2$)$_n$(C$_6$-C$_{10}$ aryl), C$_2$-C$_6$ alkenyl, and C$_2$-C$_6$ alkynyl;
$R^2$ is H;
$R^3$ and $R^4$ are independently selected from: H, F, CF$_3$, C$_1$-C$_6$ alkyl;
or $R^3$ and $R^4$ can together form a C$_3$-C$_5$ cycloalkyl ring;
$R^5$ is a moiety of the formula:

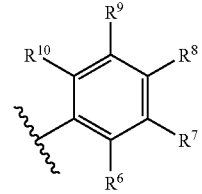

wherein $R^6$, $R^7$, $R^8$, $R^9$ and $R^{10}$ are independently selected from hydrogen, Br, Cl, F, —(CH$_2$)$_n$OR$^{11}$, —C(O)R$^{11}$, —C(O)OR$^{11}$, —C(O)NR$^{11}$R$^{12}$, —NR$^{11}$R$^{12}$, —S(O)$_2$R$^{11}$, —S(O)R$^{11}$, —S(O)$_2$NR$^{11}$R$^{12}$, —CF$_3$, —CF$_2$H, —NR$^{11}$C(O)NR$^{11}$R$^{12}$, —NR$^{11}$C(O)R$^{12}$, —NR$^{11}$SO$_2$R$^{12}$, —CN, —NO$_2$, C$_1$-C$_6$ alkyl, C$_3$-C$_8$ cycloalkyl, 3-8 membered heteroalicyclic, 8-10 membered heterobicyclic, 5-7 membered heteroaryl, C$_6$-C$_{10}$ aryl, C$_2$-C$_6$ alkenyl, and C$_2$-C$_6$ alkynyl wherein C$_1$-C$_6$ alkyl, C$_3$-C$_8$ cycloalkyl, 3-8 membered heteroalicyclic, 8-10 membered heterobicyclic, 5-7 membered heteroaryl, C$_6$-C$_{10}$ aryl, C$_2$-C$_6$ alkenyl, and C$_2$-C$_6$ alkynyl are optionally substituted by one or more moieties selected from the group consisting of Br, Cl, F, —(CH$_2$)$_n$OR$^{11}$, —C(O)R$^{11}$, —C(O)OR$^{11}$, —C(O)NR$^{11}$R$^{12}$, —NR$^{11}$R$^{12}$, —S(O)$_2$R$^{11}$, —S(O)$_2$NR$^{11}$R$^{12}$, —CF$_3$, —CF$_2$H, —NR$^{11}$C(O)NR$^{11}$R$^{12}$, —NR$^{11}$C(O)R$^{12}$, —NR$^{11}$S(O)$_2$R$^{12}$, —CN, —NO$_2$, oxo, C$_1$-C$_6$ alkyl, C$_3$-C$_8$ cycloalkyl, C$_3$-C$_8$ heteroalicyclic, 5-7 membered heteroaryl, C$_6$-C$_{10}$ aryl, C$_2$-C$_6$ alkenyl, and C$_2$-C$_6$ alkynyl; or R$^8$ and R$^9$, or R$^9$ and R$^{10}$ combine to form a ring selected from saturated C$_4$-C$_8$ cycloalkyl, unsaturated C$_5$-C$_8$ cycloalkyl, 3-8 membered heteroalicyclic, 5-7 membered heteroaryl and C$_6$-C$_{10}$ aryl, wherein said ring is optionally substituted by one or more moieties selected from the group consisting of Br, Cl, F, —(CH$_2$)$_n$OR$^{11}$, —C(O)R$^{11}$, —C(O)OR$^{11}$, —C(O)NR$^{11}$R$^{12}$, —NR$^{11}$R$^{12}$, —S(O)$_2$R$^{11}$, —S(O)R$^{11}$, —S(O)$_2$NR$^{11}$R$^{12}$, —CF$_3$, —CF$_2$H, —NR$^{11}$C(O)NR$^{11}$R$^{12}$, —NR$^{11}$C(O)R$^{12}$, —NR$^{11}$S(O)$_2$R$^{12}$, —CN, —NO$_2$, oxo, C$_1$-C$_6$ alkyl, C$_3$-C$_8$ cycloalkyl, C$_3$-C$_8$ heteroalicyclic, 5-7 membered heteroaryl, C$_6$-C$_{10}$ aryl, C$_2$-C$_6$ alkenyl, and C$_2$-C$_6$ alkynyl;

R$^{11}$ and R$^{12}$ are independently selected from H, —(CH$_2$)$_n$OR$^{13}$, —(CH$_2$)$_n$C(CH$_3$)$_2$OR$^{13}$, —CHR$^{13}$(CH$_2$)$_n$OR$^{14}$, —C(O)OR$^{13}$, —(CH$_2$)$_n$CHR$^{13}$OR$^{14}$, —C(CH$_3$)$_2$(CH$_2$)$_n$OR$^{13}$, —CH$_2$CF$_2$H, —(CH$_2$)$_n$C(CH$_3$)$_2$NR$^{13}$R$^{14}$, —(CH$_2$)$_n$NR$^{13}$R$^{14}$, —(CH$_2$)$_n$CHOR$^{13}$(CH$_2$)$_n$OR$^{14}$, —(CH$_2$)$_n$(NR$^{13}$R$^{14}$)C(O)NR$^{13}$R$^{14}$, —(CH$_2$)$_n$S(O)$_2$R$^{13}$, —(CH$_2$)$_n$C(O)NR$^{13}$R$^{14}$, —NR$^{13}$(CH$_2$)$_n$(5-7 membered heteroaryl), —NR$^{13}$(CH$_2$)$_n$(3-8 membered heterocycle), —(CH$_2$)$_n$(8-10 membered heterobicyclic), —(CH$_2$)$_n$(3-8 membered heteroalicyclic), C$_1$-C$_6$ alkyl, C$_3$-C$_8$ cycloalkyl, C$_6$-C$_{10}$ aryl, C$_2$-C$_6$ alkenyl and C$_2$-C$_6$ alkynyl, wherein said 5-7 membered heteroaryl, 3-8 membered heterocycle and 8-10 membered heterobicyclic are optionally substituted by one or more moieties selected from the group consisting of —(CH$_2$)$_n$OR$^{13}$, C$_1$-C$_6$ alkyl, C$_3$-C$_8$ cycloalkyl, C$_6$-C$_{10}$ aryl, C$_2$-C$_6$ alkenyl, 3-8 membered heteroalicyclic and C$_2$-C$_6$ alkynyl; or when R$^{11}$ and R$^{12}$ are attached to the same atom, R$^{11}$ and R$^{12}$ optionally combine to form a 3-8 membered heteroalicyclic ring;

R$^{13}$ and R$^{14}$ are independently selected from H, C$_1$-C$_6$ alkyl, —C(O)CH$_3$, C$_3$-C$_8$ cycloalkyl, C$_6$-C$_{10}$ aryl, C$_2$-C$_6$ alkenyl, 5-7 membered heteroaryl and C$_2$-C$_6$ alkynyl, wherein said 5-7 membered heteroaryl is optionally substituted by one or more moieties selected from the group consisting of C$_1$-C$_6$ alkyl, C$_3$-C$_8$ cycloalkyl, C$_6$-C$_{10}$ aryl, C$_2$-C$_6$ alkenyl, and C$_2$-C$_6$ alkynyl; or when R$^{13}$ and R$^{14}$ are attached to the same atom, R$^{13}$ and R$^{14}$ optionally combine to form a 3-8 membered heteroalicyclic ring;

each n is independently 0, 1, 2, 3 or 4.

2. A compound of Formula II or partially deuterated Formula II:

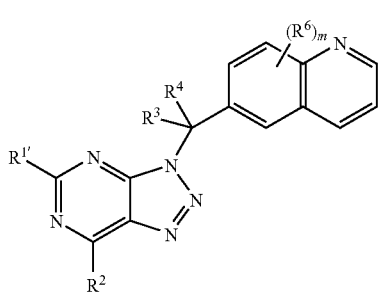

II or a pharmaceutically acceptable salt thereof, wherein

R$^{1'}$ is independently selected from hydrogen, I, Br, Cl, F, —O(CH$_2$)$_n$CH$_3$, —(CH$_2$)OR$^{11}$, —(CR$^{13}$R$^{14}$)$_n$NR$^{11}$R$^{12}$, —NR$^{11}$C(O)OR$^{13}$, —NR$^{11}$R$^{12}$, —S(O)$_2$R$^{11}$, —S(O)—R$^{11}$, —S(O)$_2$NR$^{11}$R$^{12}$, —CF$_3$, CF$_2$H, —NR$^{11}$C(O)NR$^{11}$R$^{12}$, —NR$^{11}$C(O)R$^{12}$, —NR$^{11}$S(O)$_2$R$^{12}$, —N(CH$_2$)$_n$(C$_3$-C$_8$ cycloalkyl), —CN, —NO$_2$, C$_1$-C$_6$ alkyl or R$^1$;

R$^1$ is independently selected from —O(CH$_2$)$_n$OR$^{11}$, —C(O)R$^{11}$, —C(O)OR$^{11}$, —C(O)N$^{11}$R$^{12}$, C$_3$-C$_8$ cycloalkyl, 3-8 membered heteroalicyclic, 3-8 membered heteroalicyclic-(3-8 membered heteroalicyclic), 8-10 membered heterobicyclic, 5-7 membered heteroaryl, C$_6$-C$_{10}$ aryl, C$_2$-C$_6$ alkenyl, and C$_2$-C$_6$ alkynyl wherein C$_3$-C$_8$ cycloalkyl, 3-8 membered heteroalicyclic, 8-10 membered heterobicyclic, 5-7 membered heteroaryl, C$_6$-C$_{10}$ aryl, C$_2$-C$_6$ alkenyl, and C$_2$-C$_6$ alkynyl are optionally substituted by one or more moieties selected from the group consisting of Br, Cl, F, —(CH$_2$)$_n$CH(OR$^{11}$)CH$_3$, —(CH$_2$)$_n$OR$^{11}$, —(CH$_2$)$_n$C(CH$_3$)$_2$OR$^{11}$, —C(O)R$^{11}$, —O(O)OR$^{11}$, —(CR$^{11}$R$^{12}$)$_n$C(O)OR$^{11}$, —C(O)NR$^{11}$R$^{12}$, —(CR$^{11}$R$^{12}$)$_n$C(O)NR$^{11}$R$^{12}$, —(CH$_2$)$_n$NR$^{11}$R$^{12}$, —S(O)$_2$R$^{11}$, —S(O)R$^{11}$, —S(O)$_2$NR$^{11}$R$^{12}$, —CF$_3$, —CF$_2$H, —(CH$_2$)$_n$NR$^{11}$C(O)NR$^{11}$R$^{12}$, —(CH$_2$)$_n$NR$^{11}$C(O)OR$^{12}$, —NR$^{11}$C(O)R$^{12}$, —NR$^{11}$C(O)OR$^{12}$, —NR$^{11}$S(O)$_2$R$^{12}$, —CN, —NO$_2$, oxo, C$_1$-C$_6$ alkyl, C$_3$-C$_8$ cycloalkyl, —(CH$_2$)$_n$(3-8 membered heteroalicyclic), —(CH$_2$)$_n$(5-7 membered heteroaryl), —(CH$_2$)$_n$(C$_6$-C$_{10}$ aryl), C$_2$-C$_6$ alkenyl, and C$_2$-C$_6$ alkynyl;

R$^2$ is H;

R$^3$ and R$^4$ are independently selected from H, F, CF$_3$, C$_1$-C$_6$ alkyl;

or R$^3$ and R$^4$ can together form a C$_3$-C$_5$ cycloalkyl ring;

R$^6$ is independently selected from hydrogen, Br, Cl, F, —(CH$_2$)$_n$OR$^{11}$, —C(O)R$^{11}$, —C(O)OR$^{11}$, —C(O)NR$^{11}$R$^{12}$, —NR$^{11}$R$^{12}$, —S(O)$_2$R$^{11}$, —S(O)R$^{11}$, —S(O)$_2$NR$^{11}$R$^{12}$, —CF$_3$, —CF$_2$H, —NR$^{11}$C(O)NR$^{11}$R$^{12}$, —NR$^{11}$C(O)R$^{12}$, —NR$^{11}$SO$_2$R$^{12}$, —CN, —NO$_2$, C$_1$-C$_6$ alkyl, C$_3$-C$_8$ cycloalkyl, 3-8 membered heteroalicyclic, 8-10 membered heterobicyclic, 5-7 membered heteroaryl, C$_6$-C$_{10}$ aryl, C$_2$-C$_6$ alkenyl, and C$_2$-C$_6$ alkynyl wherein C$_1$-C$_6$ alkyl, C$_3$-C$_8$ cycloalkyl, 3-8 membered heteroalicyclic, 8-10 membered heterobicyclic, 5-7 membered heteroaryl, C$_6$-C$_{10}$ aryl, C$_2$-C$_6$ alkenyl, and C$_2$-C$_6$ alkynyl are optionally substituted by one or more moieties selected from the group consisting of Br, Cl, F, —(CH$_2$)$_n$OR$^{11}$, —C(O)R$^{11}$, —C(O)OR$^{11}$, —C(O)NR$^{11}$R$^{12}$, —NR$^{11}$R$^{12}$, —S(O)$_2$R$^{11}$, —S(O)R$^{11}$, —S(O)$_2$NR$^{11}$R$^{12}$, —CF$_3$, —CF$_2$H, —NR$^{11}$C(O)NR$^{11}$R$^{12}$, —NR$^{11}$C(O)R$^{12}$, —NR$^{11}$S(O)$_2$R$^{12}$, —CN, —NO$_2$, oxo, C$_1$-C$_6$ alkyl, C$_3$-C$_8$ cycloalkyl, C$_3$-C$_8$ heteroalicyclic, 5-7 membered heteroaryl, C$_6$-C$_{10}$ aryl, C$_2$-C$_6$ alkenyl, and C$_2$-C$_6$ alkynyl;

wherein if m is greater than 1, then each R$^6$ is independently selected from hydrogen, Br, Cl, F, —(CH$_2$)$_n$OR$^{11}$, —C(O)R$^{11}$, —C(O)OR$^{11}$, —C(O)NR$^{11}$R$^{12}$, —NR$^{11}$R$^{12}$, —S(O)$_2$R$^{11}$, —S(O)R$^{11}$, —S(O)$_2$NR$^{11}$R$^{12}$, —CF$_3$, —CF$_2$H, —NR$^{11}$C(O)NR$^{11}$R$^{12}$, —NR$^{11}$C(O)R$^{12}$, —NR$^{11}$SO$_2$R$^{12}$, —CN, —NO$_2$, C$_1$-C$_6$ alkyl, C$_3$-C$_8$ cycloalkyl, 3-8 membered heteroalicyclic, 8-10 membered heterobicyclic, 5-7 membered heteroaryl, C$_6$-C$_{10}$ aryl, C$_2$-C$_6$ alkenyl, and C$_2$-C$_6$ alkynyl wherein C$_1$-C$_6$ alkyl, C$_3$-C$_8$ cycloalkyl, 3-8 membered heteroalicyclic, 8-10 membered heterobicyclic, 5-7 membered heteroaryl, C$_6$-C$_{10}$ aryl, C$_2$-C$_6$ alkenyl, and C$_2$-C$_6$ alkynyl are optionally substituted by one or more moieties selected from the group consisting of Br, Cl, F, —(CH$_2$)$_n$OR$^{11}$, —C(O)R$^{11}$, —C(O)OR$^{11}$, —C(O)NR$^{11}$R$^{12}$, —NR$^{11}$R$^{12}$, —S(O)$_2$R$^{11}$, —S(O)R$^{11}$, —S(O)$_2$NR$^{11}$R$^{12}$, —CF$_3$, —CF$_2$H, —NR$^{11}$C(O)NR$^{11}$R$^{12}$, —NR$^{11}$C(O)R$^{12}$, —NR$^{11}$S(O)$_2$R$^{12}$, —CN, —NO$_2$, oxo, C$_1$-C$_6$ alkyl, C$_3$-C$_8$ cycloalkyl, C$_3$-C$_8$ heteroalicyclic, 5-7 membered heteroaryl, C$_6$-C$_{10}$ aryl, C$_2$-C$_6$ alkenyl, and C$_2$-C$_6$ alkynyl;

R$^{11}$ and R$^{12}$ are independently selected from H, —(CH$_2$)$_n$OR$^{13}$, —(CH$_2$)$_n$C(CH$_3$)$_2$OR$^{13}$, —CHR$^{13}$(CH$_2$)$_n$OR$^{14}$, —C(O)OR$^{13}$, —(CH$_2$)$_n$CHR$^{13}$OR$^{14}$, —C(CH$_3$)$_2$(CH$_2$)$_n$OR$^{13}$, —CH$_2$CF$_2$H, —(CH$_2$)$_n$C(CH$_3$)$_2$NR$^{13}$R$^{14}$, —(CH$_2$)$_n$NR$^{13}$R$^{14}$, —(CH$_2$)$_n$CHOR$^{13}$(CH$_2$)$_n$OR$^{14}$, —(CH$_2$)$_n$(NR$^{13}$R$^{14}$)C(O)NR$^{13}$R$^{14}$, —(CH$_2$)$_n$S(O)$_2$R$^{13}$, —(CH$_2$)$_n$C(O)NR$^{13}$R$^{14}$, —NR$^{13}$(CH$_2$)$_n$(5-7 membered heteroaryl), —NR$^{13}$(CH$_2$)$_n$(3-8 membered heterocycle), —(CH$_2$)$_n$(8-10 membered heterobicyclic), —(CH$_2$)$_n$(3-8 membered heteroalicyclic), C$_1$-C$_6$ alkyl, C$_3$-C$_8$ cycloalkyl, C$_6$-C$_{10}$ aryl, C$_2$-C$_6$ alkenyl and C$_2$-C$_6$ alkynyl, wherein said 5-7 membered heteroaryl, 3-8 membered heterocycle and 8-10 membered heterobicyclic are optionally substituted by one or more moieties selected from the group consisting of —(CH$_2$)$_n$OR$^{13}$, C$_1$-C$_6$ alkyl, C$_3$-C$_8$ cycloalkyl, C$_6$-C$_{10}$ aryl, C$_2$-C$_6$ alkenyl, 3-8 membered heteroalicyclic and C$_2$-C$_6$ alkynyl; or when R$^{11}$ and R$^{12}$ are attached to the same atom, R$^{11}$ and R$^{12}$ optionally combine to form a 3-8 membered heteroalicyclic ring;

R$^{13}$ and R$^{14}$ are independently selected from H, C$_1$-C$_6$ alkyl, —C(O)CH$_3$, C$_3$-C$_8$ cycloalkyl, C$_6$-C$_{10}$ aryl, C$_2$-C$_6$ alkenyl, 5-7 membered heteroaryl and C$_2$-C$_6$ alkynyl, wherein said 5-7 membered heteroaryl is optionally substituted by one or more moieties selected from the group consisting of C$_1$-C$_6$ alkyl, C$_3$-C$_8$ cycloalkyl, C$_6$-C$_{10}$ aryl, C$_2$-C$_6$ alkenyl, and C$_2$-C$_6$ alkynyl; or when R$^{13}$ and R$^{14}$ are attached to the same atom, R$^{13}$ and R$^{14}$ optionally combine to form a 3-8 membered heteroalicyclic ring;

m is 0, 1, 2, 3, 4 or 5.

3. The compound of claim 2, wherein R$^{1'}$ is R$^{1}$.

4. The compound of claim 1, wherein R$^{1}$ is independently selected from —C(O)NR$^{11}$R$^{12}$, 3-8 membered heteroalicyclic, 3-8 membered heteroalicyclic-(3-8 membered heteroalicyclic), 8-10 membered heterobicyclic, 5-7 membered heteroaryl, C$_6$-C$_{10}$ aryl and C$_2$-C$_6$ alkenyl, wherein 3-8 membered heteroalicyclic, 3-8 membered heteroalicyclic-(3-8 membered heteroalicyclic), 8-10 membered heterobicyclic, 5-7 membered heteroaryl, C$_6$-C$_{10}$ aryl and C$_2$-C$_6$ alkenyl are optionally substituted by one or more moieties selected from the group consisting of Br, Cl, F, —(CH$_2$)$_n$CH(OR$^{11}$)CH$_3$, —(CH$_2$)$_n$OR$^{11}$, —(CH$_2$)$_n$C(CH$_3$)$_2$OR$^{11}$, —(CH$_2$)$_n$(3-8 membered heteroalicyclic), —C(O)R$^{11}$, —C(O)OR$^{11}$, —(CR$^{11}$R$^{12}$)$_n$C(O)OR$^{11}$, —C(O)NR$^{11}$R$^{12}$, —(CR$^{11}$R$^{12}$)$_n$C(O)NR$^{11}$R$^{12}$, —(CH$_2$)$_n$NR$^{11}$R$^{12}$, —S(O)$_2$R$^{11}$, —S(O)R$^{11}$, —S(O)$_2$NR$^{11}$R$^{12}$, —CF$_3$, —CF$_2$H, —(CH$_2$)$_n$NR$^{11}$C(O)NR$^{11}$R$^{12}$, —(CH$_2$)$_n$NR$^{11}$C(O)OR$^{12}$, —NR$^{11}$C(O)R$^{12}$, —NR$^{11}$C(O)OR$^{12}$, —NR$^{11}$S(O)$_2$R$^{12}$, —CN, —NO$_2$, oxo, C$_1$-C$_6$ alkyl, C$_3$-C$_8$ cycloalkyl, —(CH$_2$)$_n$(3-8 membered heteroalicyclic), —(CH$_2$)$_n$(5-7 membered heteroaryl), —(CH$_2$)$_n$(C$_6$-C$_{10}$ aryl), C$_2$-C$_6$ alkenyl, and C$_2$-C$_6$ alkynyl.

5. The compound according to claims 1 and 4, wherein R$^{8}$ and R$^{9}$ combine to form a ring selected from saturated C$_4$-C$_8$ cycloalkyl, unsaturated C$_5$-C$_8$ cycloalkyl, 3-8 membered heteroalicyclic, 5-7 membered heteroaryl and C$_6$-C$_{10}$ aryl, wherein said ring is optionally substituted by one or more moieties selected from the group consisting of Br, Cl, F, —(CH$_2$)$_n$OR$^{11}$, —C(O)R$^{11}$, —C(O)OR$^{11}$, —C(O)NR$^{11}$R$^{12}$, —NR$^{11}$R$^{12}$, —S(O)$_2$R$^{11}$, —S(O)R$^{11}$, —S(O)$_2$NR$^{11}$R$^{12}$, —CF$_3$, —CF$_2$H, —NR$^{11}$C(O)NR$^{11}$R$^{12}$, —NR$^{11}$C(O)R$^{12}$, —NR$^{11}$S(O)$_2$R$^{12}$, —CN, —NO$_2$, oxo, C$_1$-C$_6$ alkyl, C$_3$-C$_8$ cycloalkyl, C$_3$-C$_8$ heteroalicyclic, 5-7 membered heteroaryl, C$_6$-C$_{10}$ aryl, C$_2$-C$_6$ alkenyl, and C$_2$-C$_6$ alkynyl.

6. The compound according to any one of claims 1 or 2, wherein R$^{1}$ is independently selected from 3-8 membered heteroalicyclic, 3-8 membered heteroalicyclic-(3-8 membered heteroalicyclic), 8-10 membered heterobicyclic, 5-7 membered heteroaryl, C$_6$-C$_{10}$ aryl and C$_2$-C$_6$ alkenyl, wherein 3-8 membered heteroalicyclic, 3-8 membered heteroalicyclic-(3-8 membered heteroalicyclic), 8-10 membered heterobicyclic, 5-7 membered heteroaryl, C$_6$-C$_{10}$ aryl and C$_2$-C$_6$ alkenyl are optionally substituted by one or more moieties selected from the group consisting of Br, Cl, F, —(CH$_2$)$_n$CH(OR$^{11}$)CH$_3$, —(CH$_2$)$_n$OR$^{11}$, —(CH$_2$)$_n$C(CH$_3$)$_2$OR$^{11}$, —(CH$_2$)$_n$(3-8 membered heteroalicyclic), —C(O)R$^{11}$, —C(O)OR$^{11}$, —(CR$^{11}$R$^{12}$)$_n$C(O)OR$^{11}$, —C(O)NR$^{11}$R$^{12}$, —(CR$^{11}$R$^{12}$)$_n$C(O)NR$^{11}$R$^{12}$, —(CH$_2$)$_n$NR$^{11}$R$^{12}$, —S(O)$_2$R$^{11}$, —S(O)R$^{11}$, —S(O)$_2$NR$^{11}$R$^{12}$, —CF$_3$, —CF$_2$H, —(CH$_2$)$_n$NR$^{11}$C(O)NR$^{11}$R$^{12}$, —(CH$_2$)$_n$NR$^{11}$C(O)OR$^{12}$, —NR$^{11}$C(O)R$^{12}$, —NR$^{11}$C(O)OR$^{12}$, —NR$^{11}$S(O)$_2$R$^{12}$, —CN, —NO$_2$, oxo, C$_1$-C$_6$ alkyl, C$_3$-C$_8$ cycloalkyl, —(CH$_2$)$_n$(3-8 membered heteroalicyclic), —(CH$_2$)$_n$(5-7 membered heteroaryl), —(CH$_2$)$_n$(C$_6$-C$_{10}$ aryl), C$_2$-C$_6$ alkenyl, and C$_2$-C$_6$ alkynyl.

7. The compound according to any one of claims 1 or 2, wherein R$^{3}$ is H and R$^{4}$ is methyl; or R$^{4}$ is H, and R$^{3}$ is methyl.

8. The compound according to any one of claims 1 or 2, wherein R$^{3}$ and R$^{4}$ are H.

9. The compound according to any one of claims 1 or 2, wherein R$^{5}$ is selected from

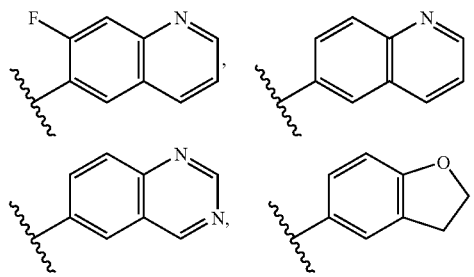

10. The compounds of claim 2, wherein said compound is selected from
   6-((5-chloro-3H-[1,2,3]triazolo[4,5-d]pyrimidin-3-yl)methyl)quinoline,
   3-(quinolin-6-ylmethyl)-3H-[1,2,3]triazolo[4,5-d]pyrimidin-5-amine,
   6-((5-iodo-3H-[1,2,3]triazolo[4,5-d]pyrimidin-3-yl)methyl)quinoline,
   6-((5-(1-methyl-1H-pyrazol-4-yl)-3H-[1,2,3]triazolo[4,5-d]pyrimidin-3-yl)methyl)quinoline,
   2-(4-(3-(quinolin-6-ylmethyl)-3H-[1,2,3]triazolo[4,5-d]pyrimidin-5-yl)-1H-pyrazol-1-yl)ethanol,
   (S)-6-(1-(5-(1-methyl-1H-pyrazol-4-yl)-3H-[1,2,3]-triazolo[4,5-d]pyrimidin-3-yl)ethyl)quinoline,
   (S)-2-(4-(3-(1-(quinolin-6-yl)ethyl)-3H-[1,2,3]triazolo[4,5-d]pyrimidin-5-yl)-1H-pyrazol-1-yl)ethanol;
   or a pharmaceutically acceptable salt thereof.

11. A pharmaceutical composition comprising a compound according to the Formula I or Formula II as defined in any one of claims 1-10 or a pharmaceutically acceptable salt thereof, and a pharmaceutical acceptable excipient.

12. A process for the preparation of a compound of claim 1 or 2, said process comprising reacting a compound of Formula VIII:

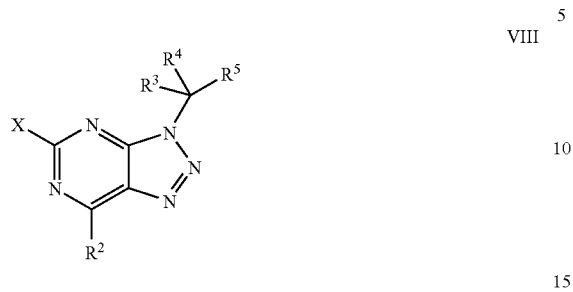

VIII with a compound of $R^1$—Y, wherein X is Cl or I or Br, and Y is zincate, boronic acid, boronate ester or stannane.

13. (S)-6-(1-(5-(1-methyl-1H-pyrazol-4-yl)-3H-[1,2,3]triazolo[4,5-d]pyrimidin-3-yl)ethyl)quinoline or a pharmaceutically acceptable salt thereof.

14. (S)-2-(4-(3-(1-(quinolin-6-yl)ethyl)-3H-[1,2,3]triazolo[4,5-d]pyrimidin-5-yl)-1H-pyrazol-1-yl)ethanol or a pharmaceutically acceptable salt thereof.

* * * * *